(12) United States Patent
McGinnis et al.

(10) Patent No.: US 8,550,080 B2
(45) Date of Patent: *Oct. 8, 2013

(54) CUSHION FOR A PATIENT INTERFACE

(75) Inventors: Gerald E. McGinnis, Export, PA (US); Peter Chi Fai Ho, Pittsburgh, PA (US); Eugene N. Scarberry, Trafford, PA (US); Lance Busch, Trafford, PA (US); Joseph M. Miceli, Jr., Pittsburgh, PA (US)

(73) Assignee: Ric Investments, LLC, Wilmington, DE (US)

( * ) Notice: Subject to any disclaimer, the term of this patent is extended or adjusted under 35 U.S.C. 154(b) by 901 days.

This patent is subject to a terminal disclaimer.

(21) Appl. No.: 12/114,132

(22) Filed: May 2, 2008

(65) Prior Publication Data

US 2008/0302366 A1 Dec. 11, 2008

Related U.S. Application Data

(60) Provisional application No. 60/915,495, filed on May 2, 2007.

(51) Int. Cl.
*A62B 18/08* (2006.01)

(52) U.S. Cl.
USPC .................................................. 128/206.24

(58) Field of Classification Search
USPC ............ 128/206.24, 206.21, 206.28, 206.26, 128/205.25, 206.13, 206.14, 206.22, 128/203.23, 206.25, 206.27, 206.29
See application file for complete search history.

(56) References Cited

U.S. PATENT DOCUMENTS

| | | | | |
|---|---|---|---|---|
| 2,254,854 | A | * | 9/1941 | O'Connell ............... 128/206.28 |
| 2,844,826 | A | * | 7/1958 | Cheiten ........................ 4/255.11 |
| 4,768,237 | A | * | 9/1988 | Torti ............................. 4/255.05 |
| 4,907,584 | A | | 3/1990 | McGinnis |
| 5,243,971 | A | | 9/1993 | Sullivan et al. |
| 5,349,949 | A | * | 9/1994 | Schegerin ............... 128/206.24 |
| 5,974,596 | A | * | 11/1999 | Strzok ......................... 4/255.11 |
| D423,096 | S | * | 4/2000 | Kwok ....................... D24/110.1 |
| 6,629,531 | B2 | * | 10/2003 | Gleason et al. ........... 128/205.25 |
| 6,796,308 | B2 | * | 9/2004 | Gunaratnam et al. ... 128/206.24 |
| 6,951,218 | B2 | * | 10/2005 | Gradon et al. ............ 128/205.25 |
| 7,007,696 | B2 | * | 3/2006 | Palkon et al. ............. 128/207.13 |
| 7,044,130 | B2 | * | 5/2006 | Jones et al. ............... 128/206.21 |
| 7,523,754 | B2 | * | 4/2009 | Lithgow et al. .......... 128/206.24 |
| 2004/0112384 | A1 | * | 6/2004 | Lithgow et al. .......... 128/206.21 |
| 2004/0112385 | A1 | * | 6/2004 | Drew et al. ............... 128/206.21 |
| 2006/0130844 | A1 | | 6/2006 | Ho et al. |
| 2006/0225740 | A1 | | 10/2006 | Eaton et al. |
| 2006/0249160 | A1 | | 11/2006 | Scarberry et al. |
| 2006/0283461 | A1 | | 12/2006 | Lubke et al. |
| 2007/0089749 | A1 | | 4/2007 | Ho et al. |
| 2009/0133697 | A1 | * | 5/2009 | Kwok et al. ............. 128/205.25 |

* cited by examiner

*Primary Examiner* — Lynne Anderson
*Assistant Examiner* — Bradley Philips
(74) *Attorney, Agent, or Firm* — Michael W. Haas

(57) ABSTRACT

A respiratory mask is provided having cushion and a shell wherein the cushion has a frustum portion that extends towards the face of the user to provide a larger more stable and comfortable interface with a user which is better able to conform to the complex geometry of the user's face.

6 Claims, 32 Drawing Sheets

CUSHION FOR A PATIENT INTERFACE

PRIORITY CLAIM

Under the provisions of 35 U.S.C. §119(e), this application claims the benefit of U.S. provisional patent application Ser. No. 60/915,495, filed May 2, 2007, the contents of each of which are incorporated herein by reference.

BACKGROUND OF THE INVENTION

1. Field of the Invention

The present invention pertains to a respiratory patient interface used to deliver gas to a user. In particular, the present invention is related to a respiratory patient interface having a cushion with a flap having a frustum-shaped portion.

2. Description of the Related Art

Obstructive sleep apnea or OSA, obstructive sleep hypopnea, and upper airway resistance syndrome (UARS) are among a variety of known disorders characterized by episodes of complete or partial upper airway obstruction during a state of diminished consciousness, such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and UARS experience repeated, frequent arousal from sleep in response to the oxygen deprivation. The arousals result in sleep fragmentation and poor sleep continuity.

Consequences of OSA, hypopnea, and UARS may include debilitating daytime sleepiness and cognitive dysfunction, systemic hypertension, cardiac dysrythmias, pulmonary arterial hypertension and congestive heart failure. Other consequences may include a predisposition to myocardial infarction, angina pectoris, stroke, right ventricular dysfunction with cor pulmonale, carbon dioxide retention during wakefulness as well as during sleep, and continuous, reduced arterial oxygen tension. Moreover, the cognitive impairment resulting from OSA, hypopnea, and UARS puts those afflicted at elevated risk of accidents.

The pathogenesis of the airway obstruction that characterizes OSA, hypopnea, and UARS can include both anatomic and functional abnormalities of the upper airway that result in increased airflow resistance. Such abnormalities may include narrowing of the upper airway due to suction forces created during inspiration, the effect of gravity pulling the tongue back to oppose the pharyngeal wall, and insufficient muscle tone in the upper airway dilator muscles, among others. It is also believed that excessive soft tissue in the anterior and lateral neck, as commonly observed in obese persons, can apply sufficient pressure to internal structures to narrow the upper airway and restrict airflow.

Conventional treatment of OSA, hypopnea, and UARS has included surgical intervention, such as uvalopalotopharyngoplasty, gastric surgery for obesity, mandibular advancement procedures, maxillo-facial reconstruction, and tracheostomy. However, surgery potentially involves considerable risk of post-operative morbidity and mortality. In addition, the failure rate of surgery is disturbingly high. Pharmacological therapy has also been proposed to treat OSA, hypopnea, and UARS; however, results have been generally disappointing.

More recently, continuous positive airway pressure (CPAP) or bi-level positive airway pressure applied during sleep has been used to treat OSA, hypopnea, and UARS patients. Positive pressure is applied in the upper airway to splint or support the airway, thereby preventing its collapse and the resultant airway obstruction. A typical positive airway pressure device comprises a gas source (e.g., a blower, gas storage container) that delivers gas via a delivery conduit to a patient interface, such as a mask. It is also known to deliver the positive airway pressure therapy as a continuous positive airway pressure (CPAP), a variable airway pressure, such as a bi-level pressure that varies with the patient's respiratory cycle, or an auto-titrating pressure that varies with the monitored condition of the patient. Pressure support therapies are also provided to treat other medical and respiratory disorders, such as Cheynes-Stokes respiration, congestive heart failure, and stroke.

There are a multitude of patient interfaces known in the art. For instance, masks that provide a seal between the gas source and the patient are common. These interfaces may include prongs which fit into the nares of the patient, nasal masks which fit over the patient's nose, full face masks that fit over the mouth and nose, and total masks which fit over the patient's entire face. For any of these devices to be effective, two competing goals often need to be balanced: comfort and functionality. The comfort of the mask may be increased by reducing the area of contact between the mask and the patient; or use of a soft, lightweight, flexible material. In contrast, to enhance functionality, it would be preferable to construct the mask from a rigid, sturdy material with a large contact area between the mask and the patient to reduce the potential for failure.

One mask which attempts to balance the competing goals of comfort and functionality is disclosed in U.S. Pat. No. 4,907,584 ("the '584 patent"). The subject matter of which is hereby incorporated by reference. This mask has a rigid support portion and a cushion. The cushion includes a flexible flap having an L-shaped cross-section such that the flaps face approximately towards one another. Although the '584 patent has substantially advanced the art, it could still be further improved upon. For instance, it has been found that for some users, the flaps may not smoothly roll inwardly. Instead, the flaps may crumple or buckle resulting in areas that may not make an effective seal.

Another mask is disclosed in U.S. Patent Application Publication No. 2006-0130844. The subject matter of which is hereby incorporated by reference. This mask has an outer shell coupled to a cushion which includes a coupling portion, a middle portion, and a flap portion. The coupling portion couples the cushion to the outer shell; the middle portion provides clearance between the flaps and the coupling portion; and the flap portion has flaps that are inwardly directed such that they face one another. However, unlike the mask disclosed in the '584 patent, this mask includes a variety of features to vary the amount of support and/or sealing provided by the cushion to balance the competing goals of comfort and functionality locally. In some locations, more support may be required. In other areas more flexibility may be required. This application discloses several alternatives to achieve this goal. For instance, the cushion may include one or more pleats, the wall thickness may be varied to adjust the amount of support, or flexibility may be adjusted portionally about the cushion. Although an improvement, this device still utilizes inwardly directed flaps which may not form an optimum seal on some users. Instead, the flaps may tend to crumple or buckle.

The above-disclosed references disclose masks with inwardly directed flaps; however, masks are also known in the art which have flaps that are directed outwardly to form a trumpet-like shape. In U.S. patent application Ser. No. 11/585,320, the contents of which are hereby incorporated by reference, the mask includes flaps which are curved outwardly to provide additional clearance for the internal nasal pillows. Although effective, outwardly directed flaps still suffer from many of the same drawbacks noted above with respect to masks with inwardly directed flaps. Instead, the flaps will tend to buckle resulting in portions that may not make an effective seal.

Although all of these masks disclose features that enhance the art, addressing the competing goals of comfort and seal integrity continues to be a significant issue.

SUMMARY OF THE INVENTION

It is an object of the present invention to overcome one or more of the deficiencies presently found in the art. To this end, the broad teachings of an embodiment of the present invention disclose a cushion for a respiratory mask having a shell and a cushion. The cushion includes three portions: a flap portion, a middle portion, and a coupling portion. The coupling portion is configured to couple the cushion to the shell of the respiratory mask. The middle portion extends between the flap portion and the coupling. The flap portion of the present embodiment of the invention includes a shoulder portion and a frustum-shaped portion extending towards the face of the user. The frustum-shaped portion extends away from the middle portion and terminates at an opening such that the opening is non-coplanar relative to the middle portion.

In another aspect, an embodiment of the present invention discloses a respiratory mask having a shell and a cushion. The cushion includes three portions: a flap portion, a middle portion, and a coupling portion. The coupling portion is configured to couple the cushion to the shell of the respiratory mask. The middle portion extends between the flap portion and the coupling. The flap portion of the present embodiment of the invention includes a frustum-shaped portion extending from the flap portion towards the face of the user. The frustum-shaped portion extends away from the middle portion and terminates at an opening such that the opening is non-coplanar with the shoulder portion.

In another aspect, an embodiment of the present invention discloses a gas supply assembly for delivering a supply of breathing gas to a user. The gas supply includes a gas supply source such as a compressor and/or gas supply container for generating a breathing gas for use by a user. Connected to the gas supply is a conduit. The conduit is in turn connected to a respiratory mask to provide fluid communication between the gas supply source and the respiratory mask. The respiratory mask of the present invention has a shell and a cushion. The cushion includes three portions: a flap portion, a middle portion, and a coupling portion. The coupling portion is configured to couple the cushion to the shell of the respiratory mask. The middle portion extends between the flap portion and the coupling portion and provides clearance between the flap portion and the coupling portion so that the user's face does not make contact with the coupling portion. The flap portion of this embodiment includes a frustum-shaped portion extending from the shoulder portion towards the face of the user. The frustum-shaped portion terminates at an opening such that the opening is non-coplanar with the shoulder portion.

In another aspect, an embodiment of the present invention discloses a gas supply assembly for delivering a supply of breathing gas to a user. The gas supply includes a gas supply source such as a compressor and/or gas supply container for generating a breathing gas for use by a user. Connected to the gas supply is a conduit. The conduit is in turn connected to a respiratory mask to provide fluid communication between the gas supply source and the respiratory mask. The respiratory mask of the present invention has a shell and a cushion. The cushion includes three portions: a flap portion, a middle portion, and a coupling portion. The coupling portion is configured to couple the cushion to the shell of the respiratory mask. The middle portion extends between the flap portion and the coupling portion and provides clearance between the flap portion and the coupling portion so that the user's face does not make contact with the coupling portion. The flap portion of this embodiment includes a frustum-shaped portion extending from the shoulder portion towards the face of the user. The frustum-shaped portion terminates at an opening such that the opening. The frustum-shaped portion includes an apex region, corner regions, side regions, and a base region. The frustum-shaped portion extends away from the coupling portion extends with multiple different angles about the flap.

In another aspect, an embodiment of the present invention discloses a gas supply assembly for delivering a supply of breathing gas to a user. The gas supply includes a gas supply source such as a compressor and/or gas supply container for generating a breathing gas for use by a user. Connected to the gas supply is a conduit. The conduit is in turn connected to a respiratory mask to provide fluid communication between the gas supply source and the respiratory mask. The respiratory mask of the present invention has a shell and a cushion. The cushion includes three portions: a flap portion, a middle portion, and a coupling portion. The coupling portion is configured to couple the cushion to the shell of the respiratory mask. The middle portion extends between the flap portion and the coupling portion and provides clearance between the flap portion and the coupling portion so that the user's face does not make contact with the coupling portion. The flap portion of this embodiment includes a frustum-shaped portion extending from the shoulder portion towards the face of the user. The frustum-shaped portion terminates at an opening such that the opening. The frustum-shaped portion includes an apex region, corner regions, side regions, and a base region. The frustum-shaped portion extends away from the coupling portion extends with multiple different angles about the flap. The largest angle occurs at about 15 degrees to approximately 60 degrees on either side of the apex region.

In another aspect, an embodiment of the present invention discloses a cushion for a respiratory mask having a shell and a cushion. The cushion includes three portions: a flap portion, a middle portion, and a coupling portion. The coupling portion is configured to couple the cushion to the shell of the respiratory mask. The middle portion extends between the flap portion and the coupling portion. The flap portion is configured to form a seal with the face of the user and extends outwardly and inwardly away from the middle portion and terminates at an opening.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
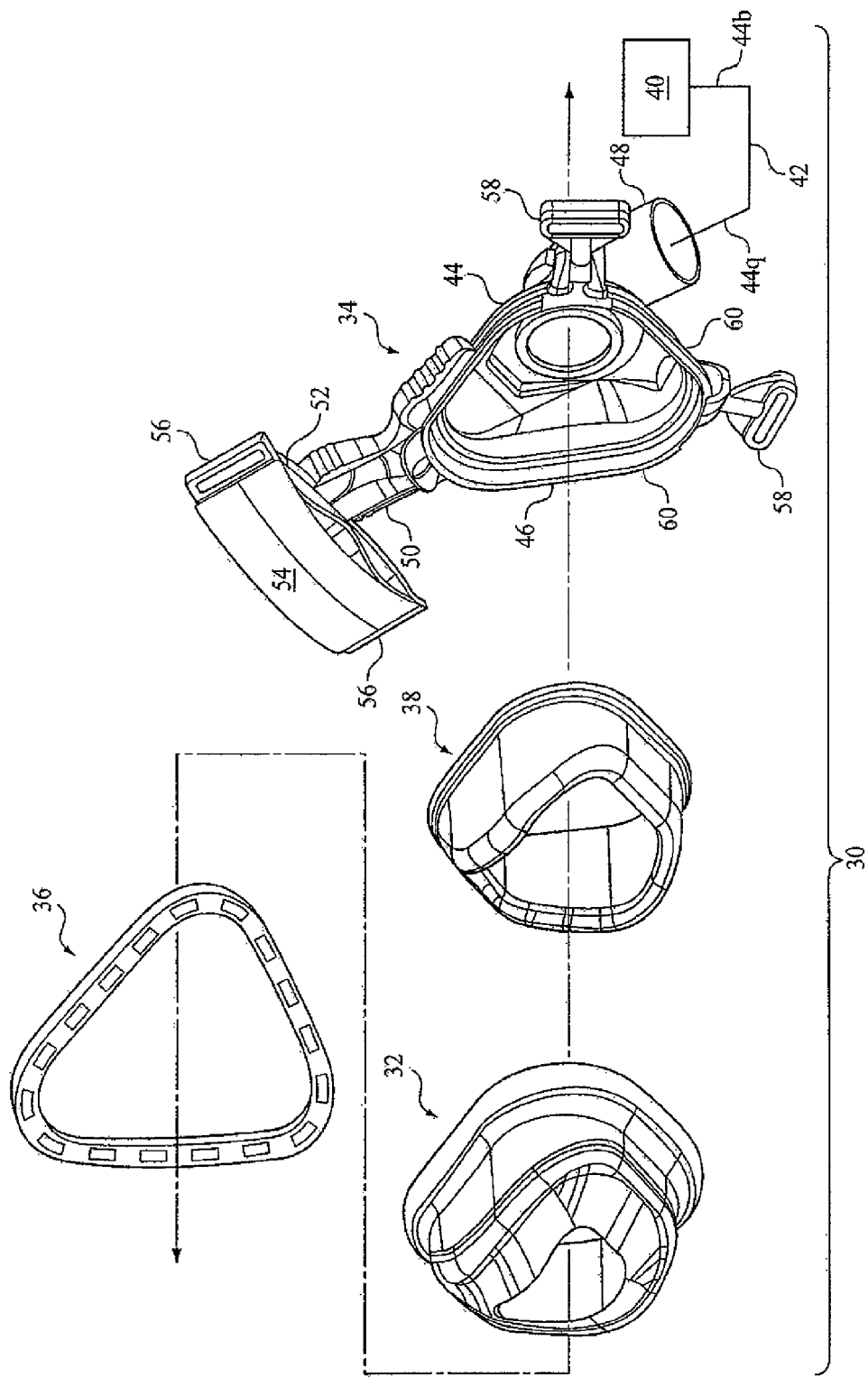
FIG. 1 is an exploded perspective view of the mask of a first embodiment of a mask according to the principles of the present invention.
Figure 2:
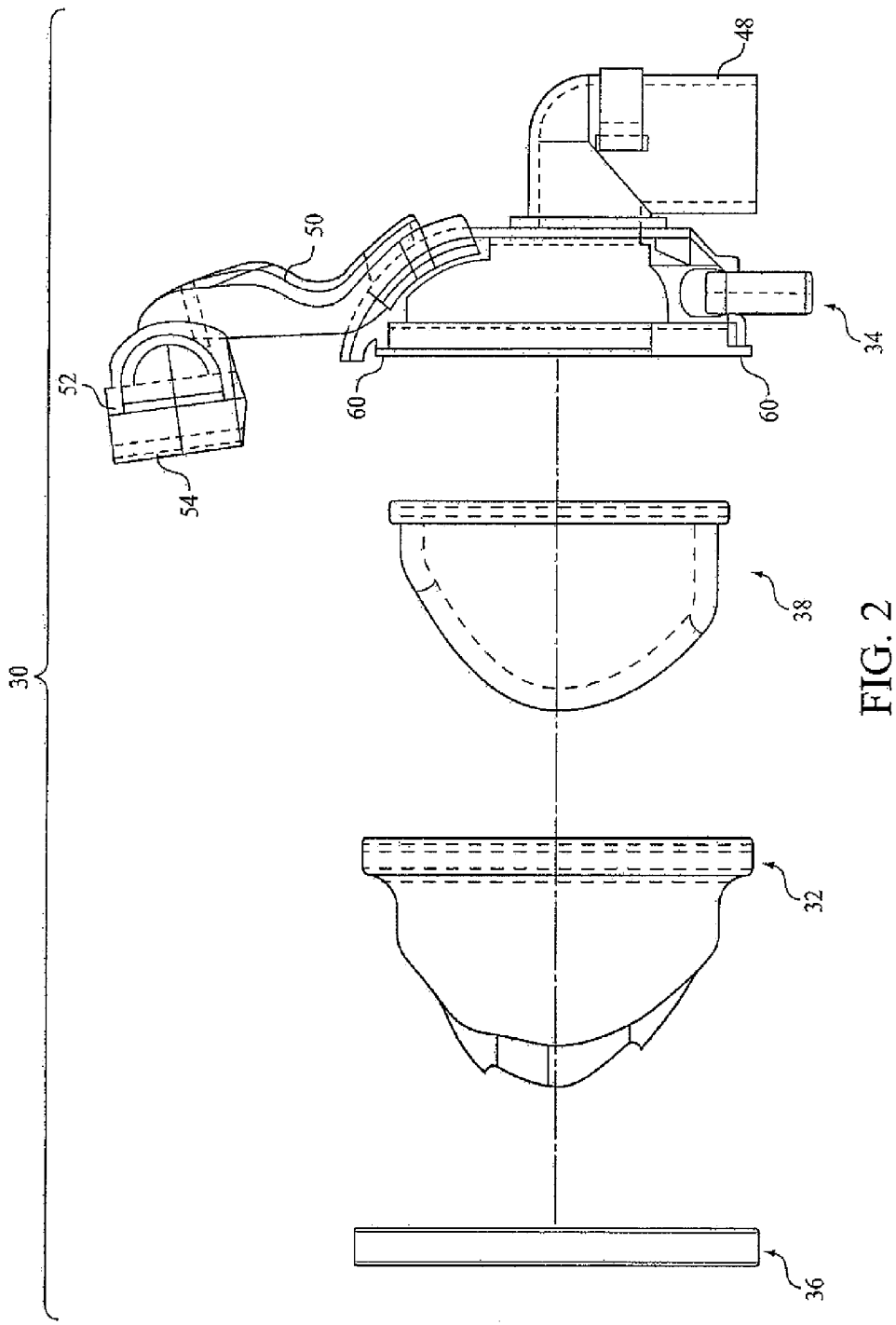
FIG. 2 is an exploded side elevational view of the mask of FIG. 1.
Figure 3:
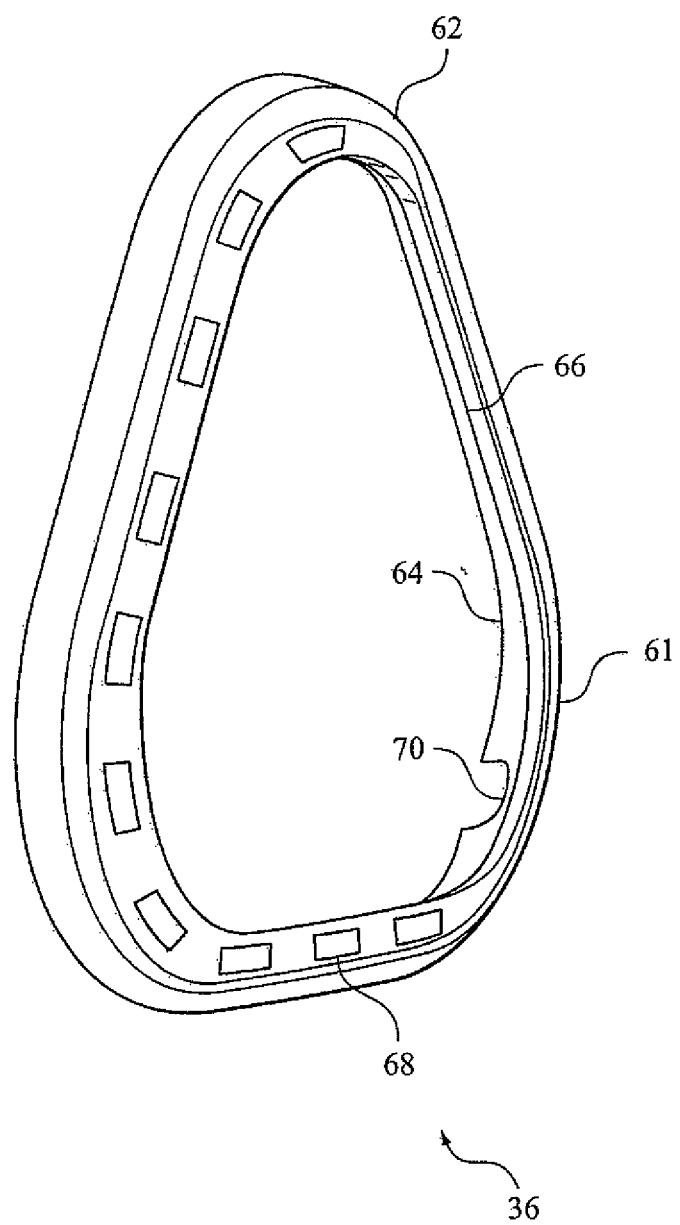
FIG. 3 is a perspective view of a mask retainer ring for the mask of FIG. 1.

FIGS. 1-3 schematically illustrates an exemplary embodiment of respiratory mask 30 according to the principles of the present invention. Mask 30 includes a cushion 32 attached to a shell 34 by a mask retention ring 36. Cushion 30 is configured to seal with the face of the patient. The retention ring fits about cushion 32 and captures a portion of the cushion between retention ring 36 and shell 34 to securely hold the cushion and the shell together. The mask also includes an insert 38 sandwiched between the cushion and the shell. The shell is connected to a gas source 40 by a conduit 42.

The gas source may be any of the compressor-type positive pressure devices known in the art including but not limited to continuous positive airway pressure, bi-level positive airway pressure, or any other similar positive pressure device. Alternatively, the gas source may generate a positive, negative or ambient pressure environment. In addition, the gas source may include alone or in combination with a compressor-type device a gas storage container providing oxygen alone or in combination with other breathing gases as deemed appropriate for use in a particular application.

The conduit may be any suitable conduit known in the art capable of providing fluid communication between a gas source and a mask. For instance, the conduit may be planar-cylindrical or corrugated tubing. The tube may be of any suitable length and diameter appropriate for the delivery of gas to a user. One end 44a of the conduit is configured to connect to the conduit coupling while the other end 44b is configured to be coupled to the gas source.

With particular reference to FIGS. 1 and 2, the shell, in one embodiment, has a generally triangular-shaped body 46 with a conduit coupling 48 connected to conduit 42. The conduit coupling is rotatable so that the tube may be oriented in any suitable direction to prevent becoming tangled or occluded while maintaining a seal with the shell. In addition, the conduit coupling may be formed to direct the conduit in any desirable angle relative to the mask. As shown, the conduit coupling is bent to form an elbow so that the tube extends approximately parallel relative to the body of the shell.

Extending from the shell is an extension, or frame, 50. The extension terminates at a forehead support 52 having a pad 54. The extension may be fixed or it may be telescopically adjustable relative to the mask so that the distance between the mask and the forehead support may be adjusted to accommodate users of different ages or facial characteristics. The forehead support may be fixed to the extension or mounted to the extension by a pivot connection. The pad is configured to contact the user's forehead to provide support and comfort to the user, and may be solid, or include a liquid or gel to enhance comfort. The device also includes ears 56 extending from the forehead support and latches 58 extending from the shell. Ears 56 in combination with latches 58 are used to secure the mask on the face of the user via a headgear assembly, not shown. The ears and latches may have a variety of configurations including but not limited to those shown in U.S. Patent Publication No. 2006-0225740. The contents of which are hereby incorporated by reference.

Ledges 60 extend outwardly about the shell are configured to interface with retention ring 36 to connect the retention ring to the shell. As seen in FIG. 3, the connection ring 36 has a generally triangular-shaped body 61 with an L-shaped cross-section defined by a top portion 62 and a skirt 64. The body 61 further includes ledges 66. The ledges are configured to captured ledges 60 to hold the retention ring in place relative to the shell. The retention ring also includes openings 68 to enhance flexibility and decrease unnecessary material utilization in the retention ring. The retention ring also includes groove 70 which further enhances flexibility and provides a convenient location to insert an object to pry the retention ring free from the shell to disassemble the mask. Cushion 32 may be connected to the shell 34 in a variety of other methods known in the art. For instance, the cushion could be attached via an adhesive. Alternatively, the cushion could be attached by overmolding the cushion onto the shell. Or, the cushion could be constructed from a single unitary structure without a separate shell.

As discussed above, the mask may include an insert 38 located between the shell and the retention ring. The insert enhances support and comfort to the user, and can be formed from a solid material or filled with a liquid, gel, any other suitable material, or combination thereof. The insert, as shown, roughly conforms to the internal contours of the cushion; however, the insert could have a variety of other configurations and could be located in a variety of other locations to enhance the support and/or the comfort of a particular portion of the mask as desired.

Turning now to the cushion shown in FIGS. 4A-7, one skilled in the art can best appreciate that cushion 32 has a unique configuration. Specifically, cushion 32 has a generally triangular-shaped body 72 configured to contact the face of the user and provide a fluid-tight seal so that the gas supplied by the gas source may be efficiently communicated to the user. Generally, the body has an apex region 74 and corner regions 76. Extending between apex region 74 and corner regions 76 are side regions 78, and extending between corner regions 76 is a base region 80. The body also has a coupling portion 82 configured to couple the cushion to the shell and a flap portion 86 configured to contact the face of the user. Between flap portion 86 and coupling portion 82 is a middle portion 84 configured to provide clearance between the flap portion and the coupling portion. To further distinguish between the various portions of the mask, the coupling portion includes a coupling apex portion 90, coupling corner portions 92, coupling side portions 94, and coupling base portion 96. The middle portion includes a middle apex portion 98, middle corner portions 100, middle side portions 102 and a middle base portion 104. The flap portion includes a flap apex portion 106, flap corner portions 108, flap side portions 110, and a flap base portion 112.

Figure 4A:
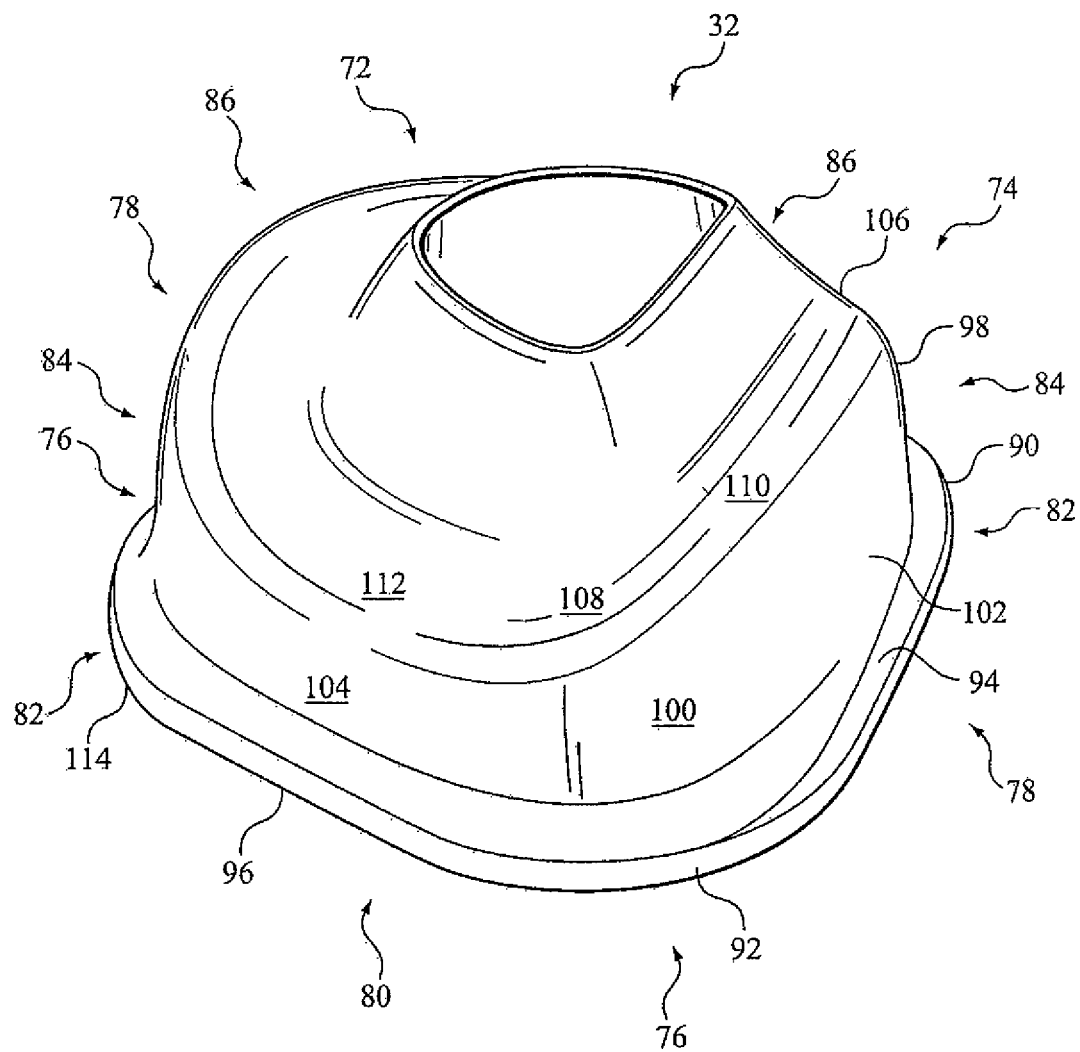
FIG. 4A, 4B, 4C, and 4D are perspective, side, front, and rear elevational views of the cushion of FIG. 1.
Figure 4B:
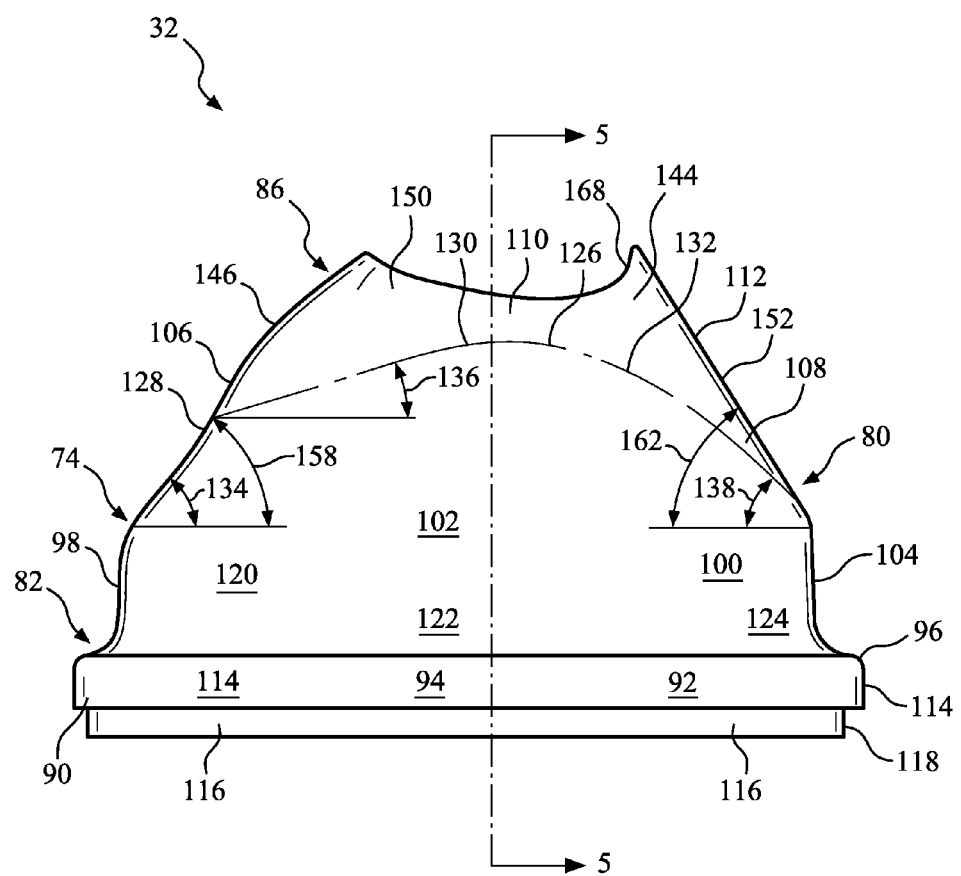

Turning to FIG. 4B, the coupling portion of the cushion has a collar 114 which is captured by the top portion 62 of the retention ring 36 to form a seal between the retention ring and the cushion. Adjacent the collar is a lip 116 radially spaced inwardly by an undercut 118 which seals with the insert. The insert, in turn, seals against the shell. Alternatively, in some embodiments, the insert may be omitted. If omitted, the lip may be configured to seal directly against the body of the shell. The middle side portion of the cushion has a generally dome-shaped configuration extending between the coupling side portion and the flap side portion. The sides 78 have an apex-proximal portion 120, a central portion 122, and a base-proximal portion 124. The height the sides 78 extend away from the coupling portion 82 is greater in the central portion 122 than in the apex-proximal portion 120 or the base-proximal portion 124.

Figure 4C:
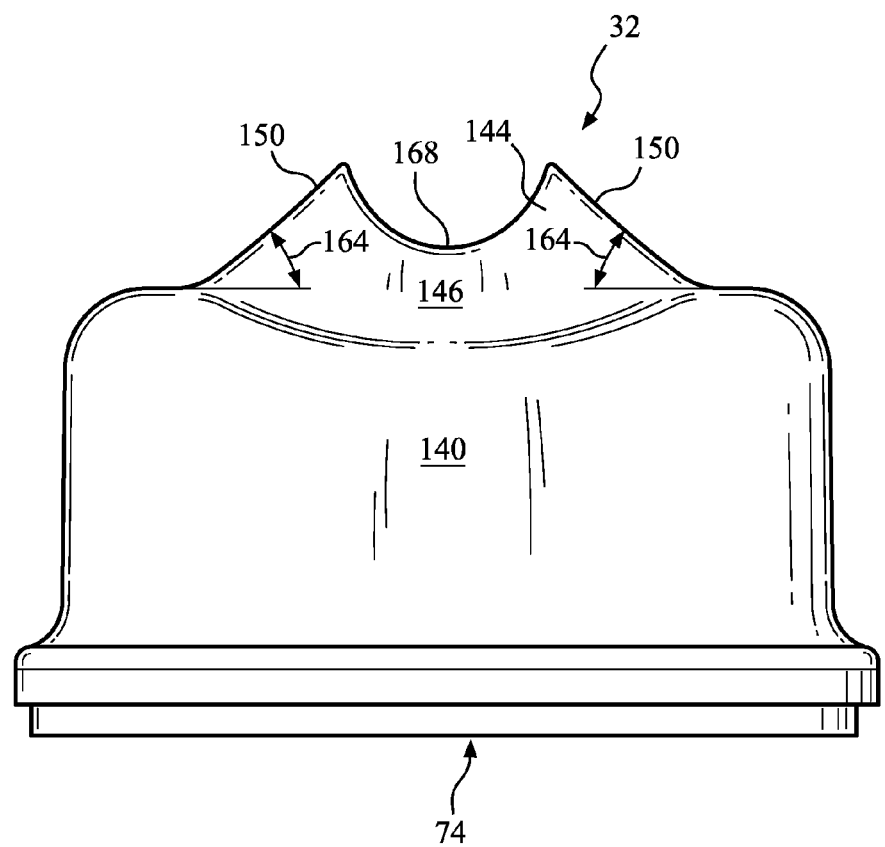
Figure 4D:
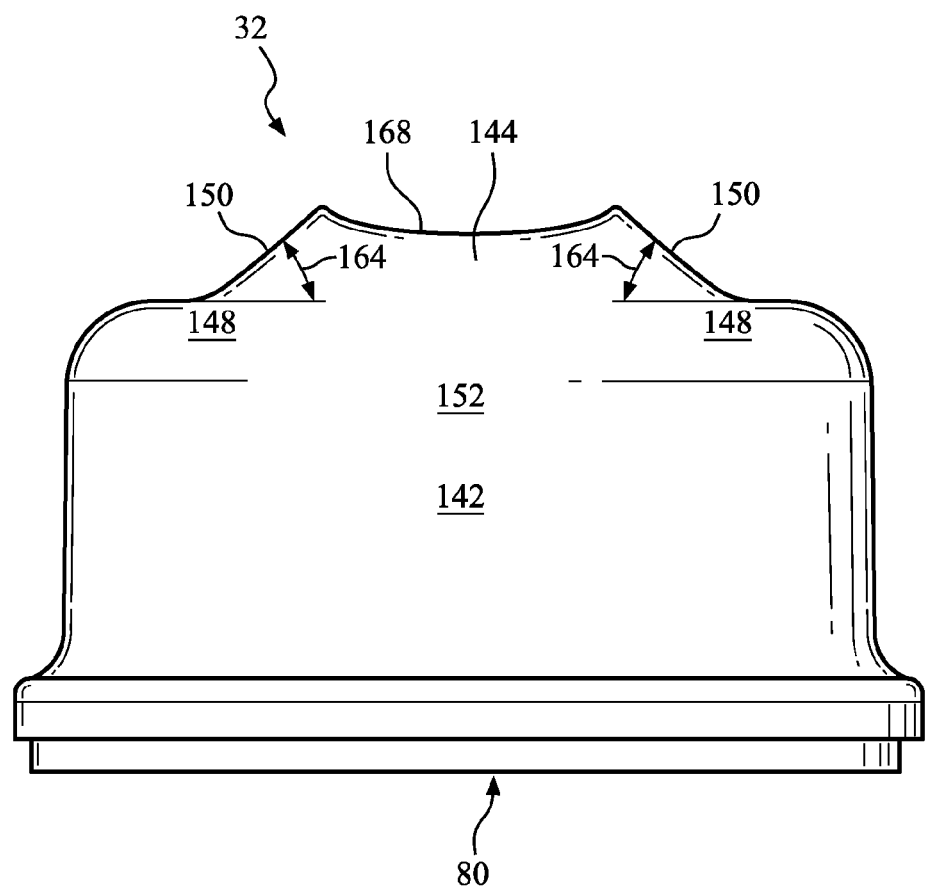

Flap portion 86 has a shoulder 126. In an exemplary embodiment, shoulder 126 is configured to roughly conform to the facial features of a user about the nasal portion to enhance the seal with the face of the user. The shoulder forms an annular ring about the cushion and traces a nonlinear path that roughly conforms to the complex geometry of the user's face. When viewed from the side, the shoulder defines an apex-proximal flap surface 128, a central flap surface 130, and a base proximal flap surface 132. Angle 136 of the central flap surface is acute. Angle 134 of the apex-proximal flap surface and angle 138 of the base-proximal flap surface 132 are also acute; however angle 134 and angle 138 are greater than angle 136. As seen in FIGS. 4C and 4D, as shoulder 126 passes around apex region 74 and base region 80, the shoulder defines an apex flap surface 140 and a base flap surface 142. The apex flap surface comes to a rounded point in the apex region while the base flap surface has a low flat U-shaped configuration in the base portion.

The flap portion includes a frustum-shaped portion 144 extending from shoulder 126 and terminating at opening 168. The frustum-shaped portion extends outwardly from the cushion and inwardly. In one embodiment, the opening is located at least ⅛ inch above the shoulder or middle portion and at least ½ inch inboard of the shoulder or middle portion. In essence, the frustum-shaped portion extends away from the shoulder and has a frustum-like shape. Of course, the frustum-shaped portion may have a variety of geometric shapes. For instance, in the present embodiment, the frustum-shaped portion has a frusta-pyramidal shape defined by a frusta-apex 146, frusta-corners 148, frusta-sides 150 and a frusta-base 152. As seen in FIGS. 4B-4D and FIG. 6, the frusta-apex 146 extends at an angle 158; frusta-base 152 extends at an angle 162; frusta-sides 150 extend upward at an angle 164; frusta-corners 148 extend at an angle 160. These angles are shown measured from the midpoint of each respective region. Of course, the angles smoothly transition from each angle to the next angle in the corresponding adjacent region.

Figure 5:
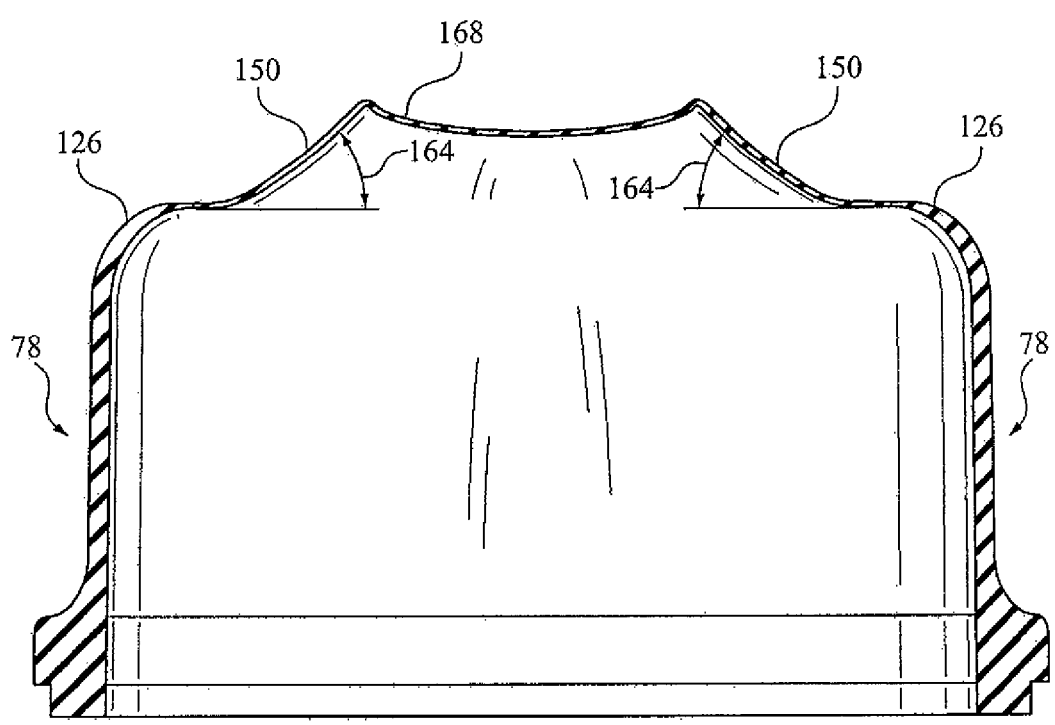
FIG. 5 is a cross-sectional view of the cushion taken along line 5-5 of FIG. 4B.

FIG. 5 shows a cross-sectional view of the cushion. As best appreciated with reference to this figure, sides 78 are substantially planar along the majority of the sides. However, one of ordinary skill in the art can best appreciate that the sides could have a wall thickness that varies to adjust the flexibility and rigidity of the cushion. In addition, the cushion could also include pleats to further adjust the flexibility and rigidity of the cushion as best appreciated with reference to pending U.S. Patent Application Publication No. 2006-0130844. The contents of which are hereby incorporated by reference.

Figure 6:
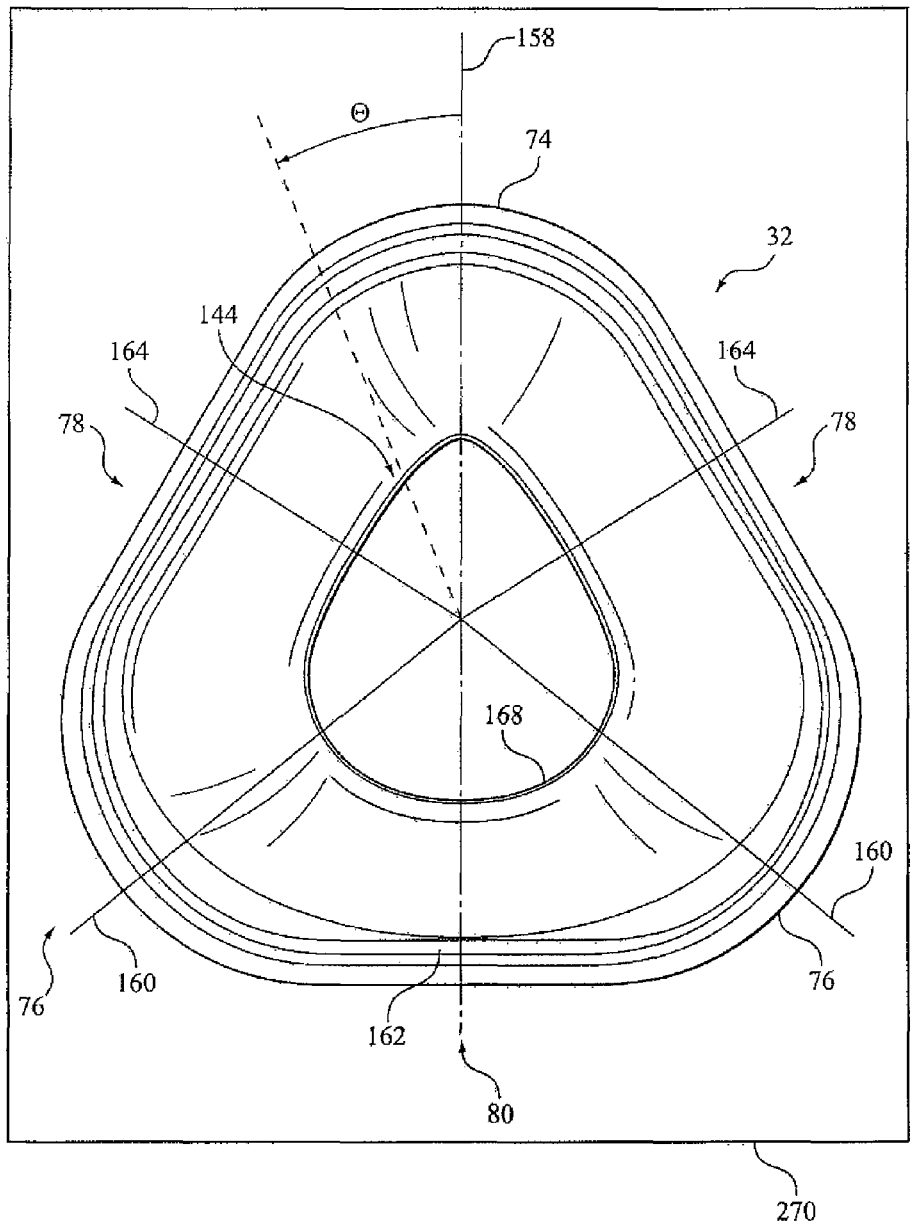
FIG. 6 is a top plan view of the cushion used in the mask of FIG. 1.
Figure 7:
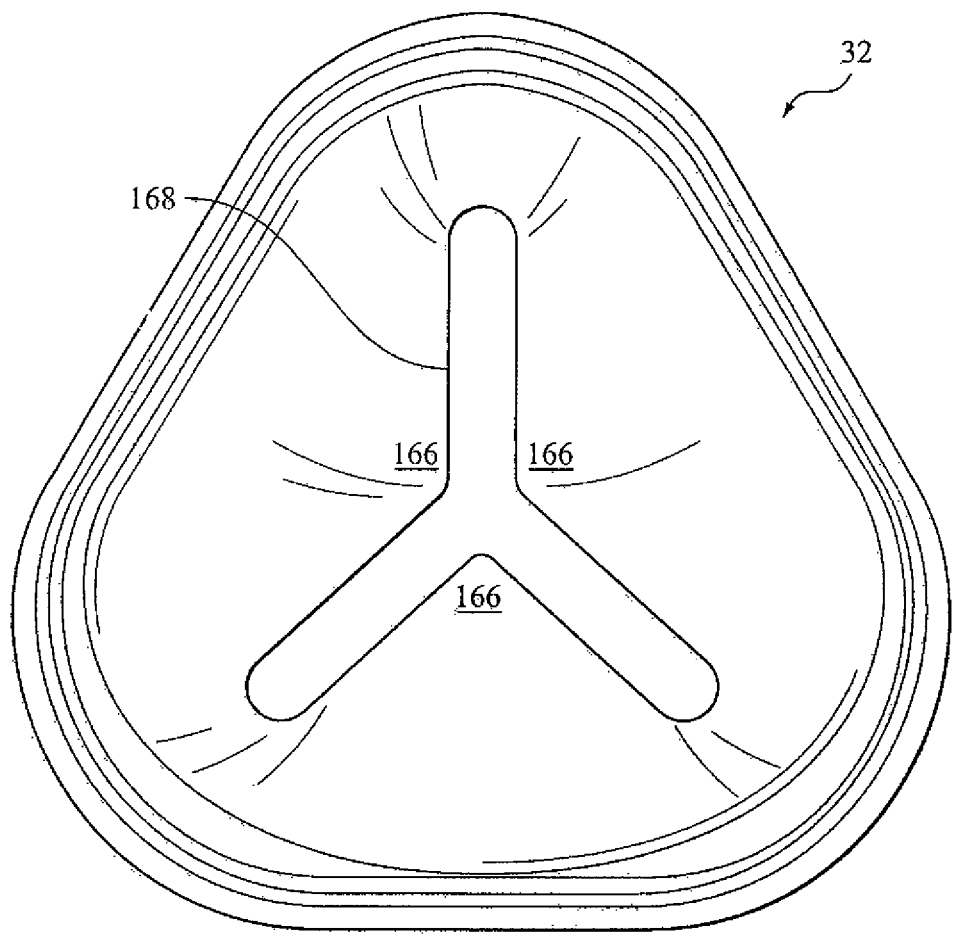
FIG. 7 is a top plan view of a second embodiment of the cushion.
Figure 8:
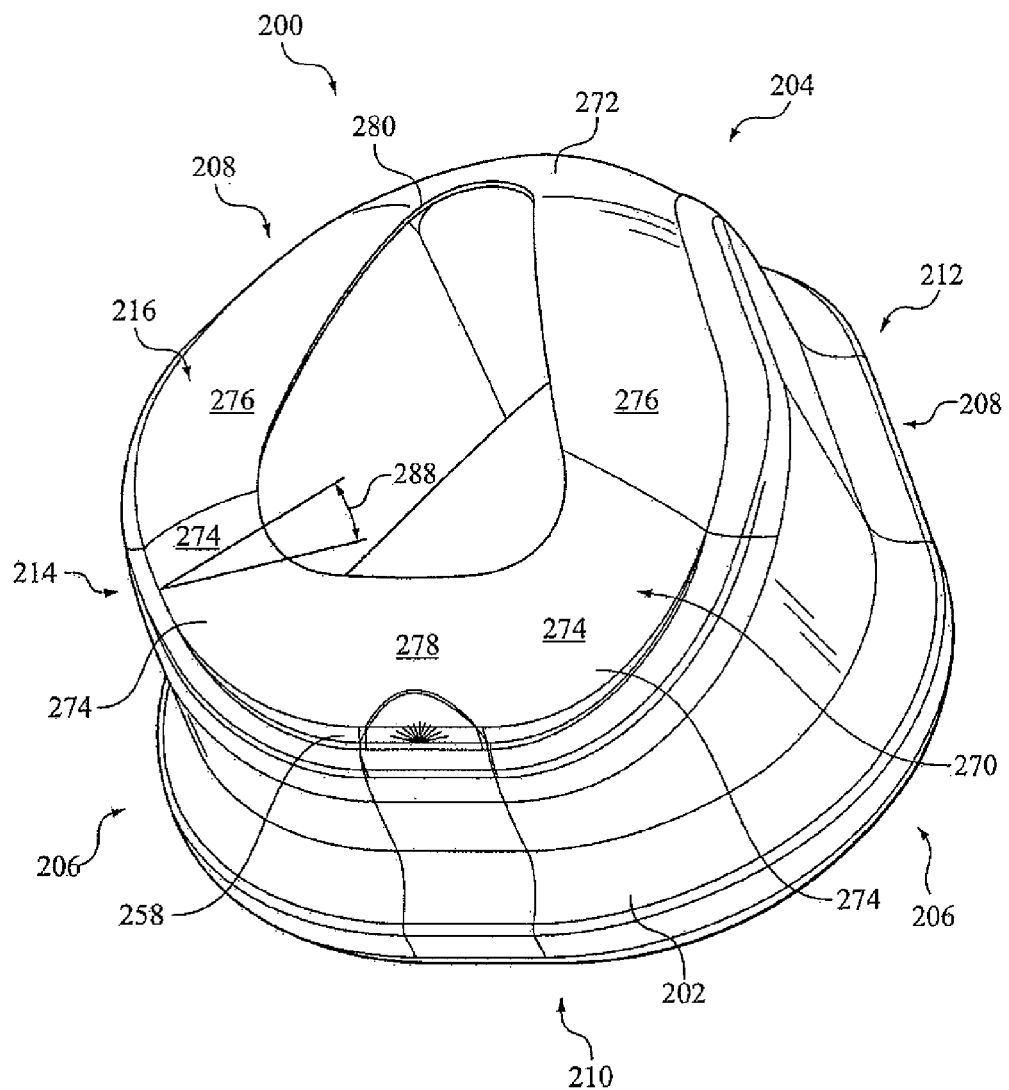
FIG. 8 is a side perspective view of a third embodiment of the cushion.
Figure 9:
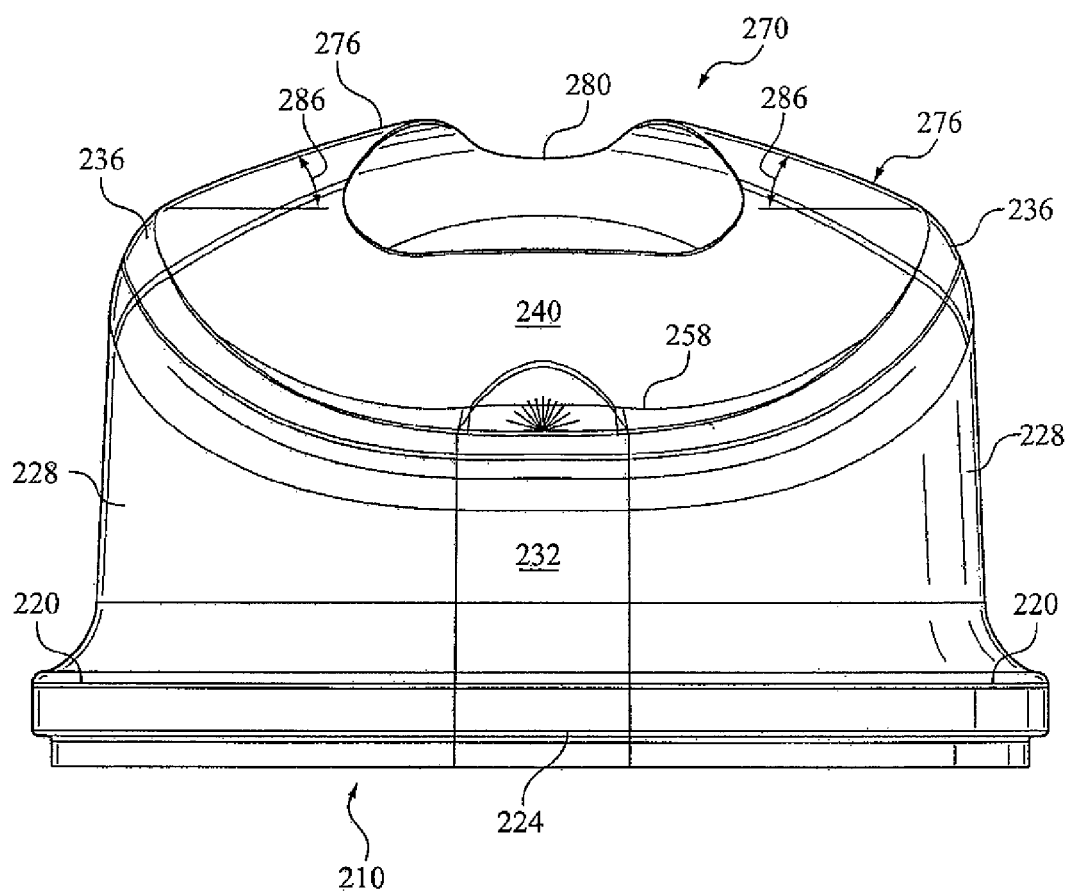
FIG. 9 is a rear elevational view of the cushion of FIG. 8.

Opening 168 may have a variety of configurations. Two different opening geometries are shown in FIG. 6 and FIG. 7. For instance, the opening may have a teardrop or triangular-shaped cutout as shown in FIG. 6. Alternatively, the opening may have a star-shaped cutout as shown in FIG. 7. The star-shaped cutout provides protruding flaps 166. Of course, the opening may have a variety of other shapes without departing from the scope of the present invention including but not limited to a circular, ovular, triangular, rectangular, or any other polygonal shape with or without protruding flaps.

An alternative embodiment of the present invention is depicted in FIGS. 8-12. This embodiment is similar to the previous embodiment except that it has a more subtle transition from the shoulder to the frustum-shaped portion, and the angles of the frustum-portions are more acute than in the previous embodiment. As in the prior embodiment, the present invention provides a cushion 200 having a generally triangular-shaped body 202 configured to contact the face of the user and provide a fluid-tight seal so that the gas supplied by the gas source may be communicated to the user. Generally, the body has an apex region 204 and corner regions 206. Extending between the apex region 204 and corner regions 206 are side regions 208. Extending between corner regions 206 is base region 210. The body also has a coupling portion 212 configured to couple the cushion to the shell and a flap portion 216 configured to contact the face of the user. Between the flap portion 216 and the coupling portion 212 is a middle portion 214 configured to provide clearance between the flap portion and the coupling portion. To further distinguish between the various portions of the mask, the coupling portion includes a coupling apex portion 218, coupling corner portions 220, coupling side portions 222, and coupling base portion 224. The middle portion includes a middle apex portion 226, middle corners 228, middle sides 230 and a middle base 232. The flap portion includes a flap apex portion 234, flap corner portions 236, flap side portions 238, and a flap base portion 240.

Figure 10:
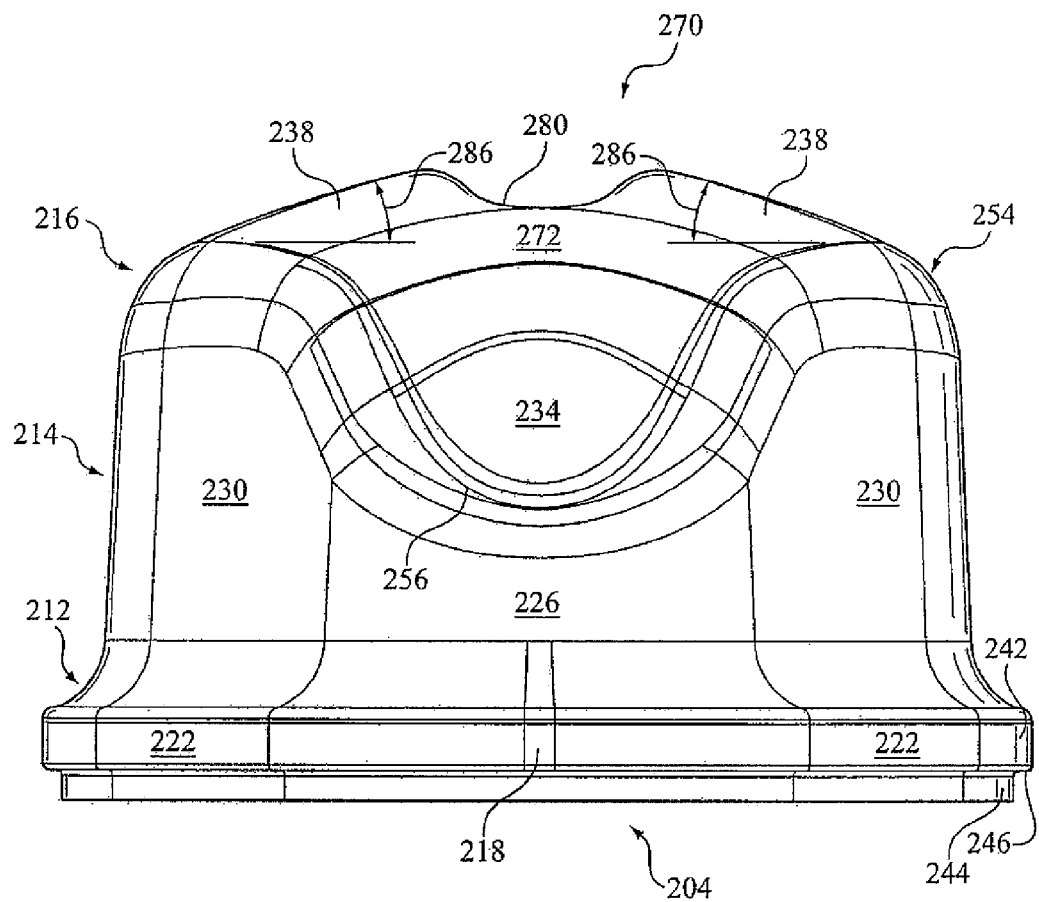
FIG. 10 is a front elevational view of the cushion of FIG. 8.
Figure 11:
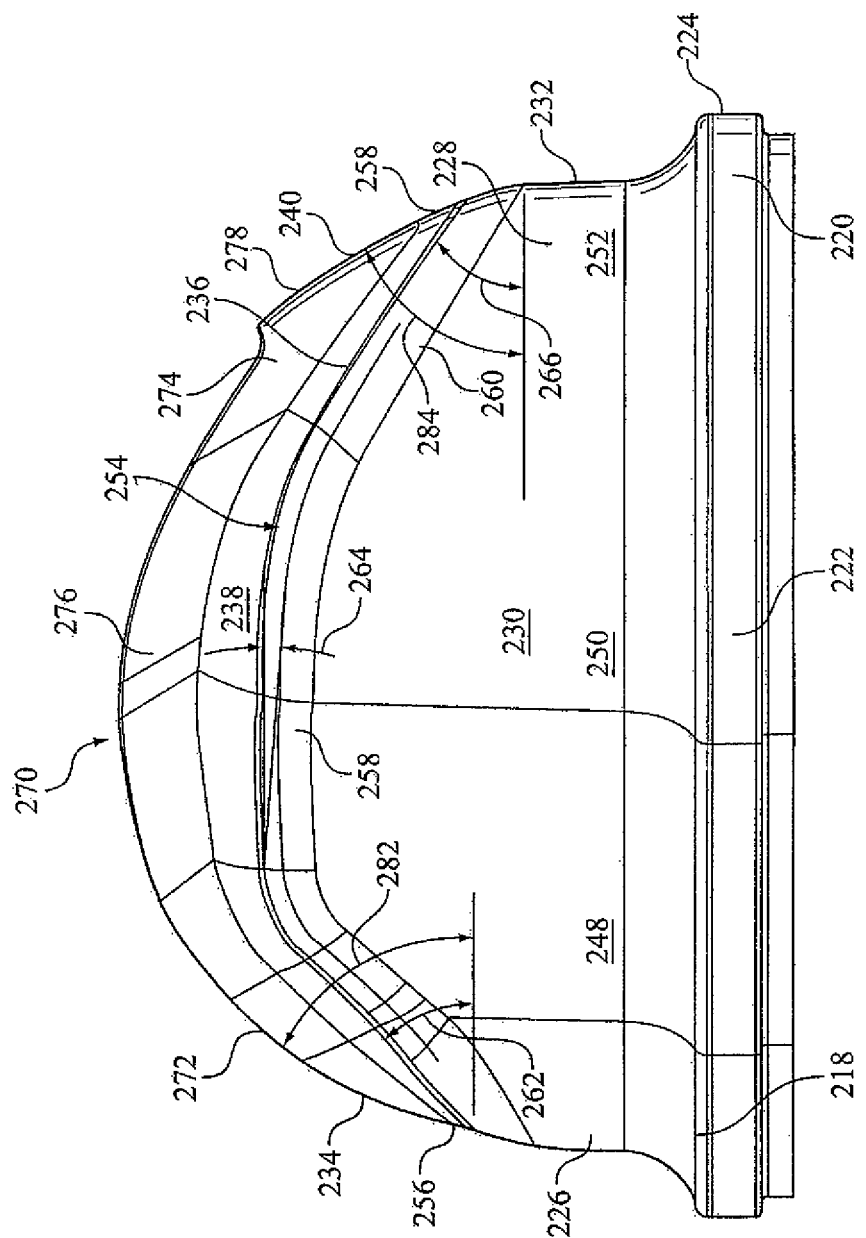
FIG. 11 is a side elevational view of the cushion of FIG. 8.

As seen in FIGS. 10 and 11, the coupling portion of the cushion has a collar 242 which is captured by the top portion 62 of the retention ring 36 to form a seal between the retention ring and the cushion (shown in FIG. 1). Adjacent the collar is a lip 244 radially spaced inwardly by an undercut 246 which seals with the insert. The insert, in turn, seals against the shell. Alternatively, in some embodiments, the insert may be omitted. If omitted, the lip may be configured to seal directly against the body of the shell. The middle side portion of the cushion has a generally dome-shaped configuration extending between the coupling side portion and the flap side portion. The sides 230 have an apex-proximal portion 248, a central portion 250, and a base-proximal portion 252. The height middle sides 230 extend away from coupling portion 212 is greater in the central portion 250 than in the apex-proximal portion 248 or the base-proximal portion 252.

With reference to FIGS. 9-12, the flap portion 216 has a shoulder 254 which is configured to roughly conform to the facial features of a user about the nasal portion to enhance the seal with the face of the user. The shoulder forms an annular ring about the cushion and traces a nonlinear path that roughly conforms to the complex geometry of the user's face. When viewed from the side, the shoulder defines an apex-proximal flap surface 256, a central flap surface 258, and a base proximal flap surface 260. Angle 264 of the central flap surface is acute. Angle 262 of the apex-proximal flap surface and angle 266 of the base-proximal flap surface 260 are also acute; however angle 262 and angle 266 are greater than angle 264. As shoulder passes around and in to apex region 204 and base portion 210, the shoulder defines an apex flap surface 256 and a base flap surface 258. The apex flap surface comes to a rounded point in the apex region while the base flap surface has a low flat U-shaped configuration in the base portion.

The flap portion of the present invention also includes a frustum-shaped portion 270 extending from shoulder 254 and terminating at opening 280 whereas prior art cushions have flap portions that terminate at the shoulder which extends approximately normal to the face of the user a short distance from the periphery of the cushion. The frustum-shaped portion extends from the shoulder and has a frustum-like shape. The frustum-shaped portion may have a variety of geometric shapes. For instance, in the present embodiment, the frustum-shaped portion has a frusta-pyramidal shape defined by a frusta-apex 272, frusta-corners 274, frusta-sides 276 and a frusta-base 278. As seen in FIGS. 8-12, the frusta-apex 272 extends at an angle 282; frusta-base 278 extends at an angle 284; frusta-sides 276 extend upward at an angle 286; and frusta-corners 274 extend at an angle 288. These angles are shown measured from the midpoint of each respective region. Of course, the angles smoothly transition from each angle to the next angle in the corresponding adjacent region.

Figure 12:
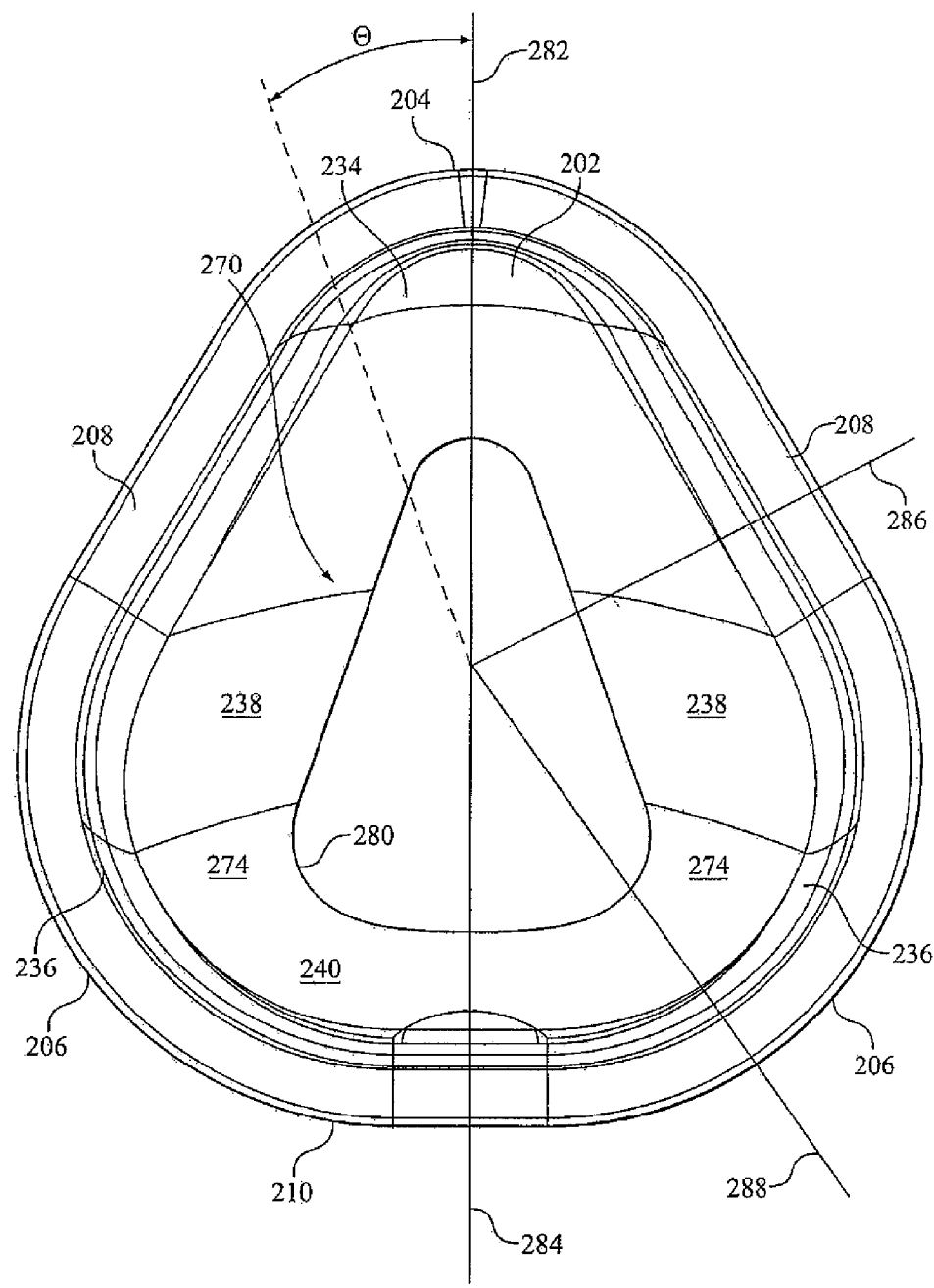
FIG. 12 is a top plan view of the cushion of FIG. 8.
Figure 13:
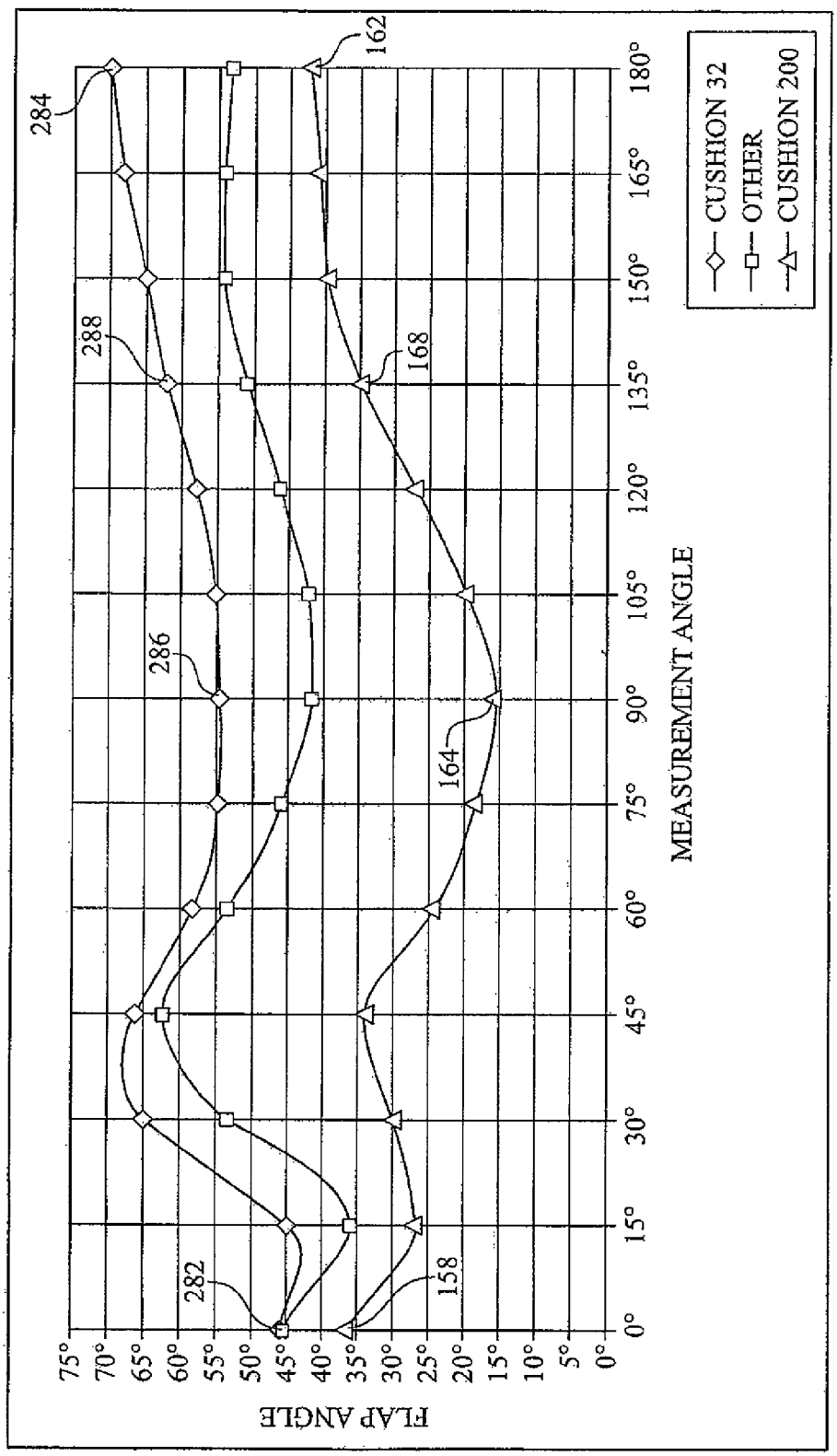
FIG. 13 is a chart depicting the flap angle for the frustum-shaped portion of the cushion of FIG. 8.

With reference to FIGS. 6, 12, and 13, one skilled in the art can appreciate that the angle of frustum-shaped portion 144, 270, varies about the respective cushion 32, 200. The angles vary continuously about the cushion as angle Θ, shown on FIGS. 6 and 12, sweeps about the mask from 0 degrees at apex regions 74, 204 to 180 degrees at the middle of base 80, 210. FIG. 13 depicts the angle for cushion 32, cushion 200, and another embodiment not shown elsewhere. One skilled in the art can appreciate that these embodiments have angles which trend in approximately the same manner but vary by degree. The angles for cushion 32 are more sever than the angles for the undepicted embodiment or cushion 200. The same data is provided below in tabular format in Table 1. While the precise angle of the frustum-portion is described in the Table 1, and FIG. 13, various other embodiments could be constructed utilizing the unique aspects of the present invention without using the precise angles described.

TABLE 1

| Angle | Cushion 32 | Other | Cushion 200 |
|---|---|---|---|
| 0 | 45.6 | 44.9 | 36.7 |
| 15 | 44.3 | 36.1 | 27.4 |
| 30 | 65.1 | 53.3 | 30 |
| 45 | 66.5 | 62.6 | 34.1 |
| 60 | 58.6 | 53.5 | 25.2 |
| 75 | 54.8 | 46.4 | 19.1 |
| 90 | 54.6 | 42.0 | 16.6 |
| 105 | 55.2 | 42.4 | 20.4 |
| 120 | 58.1 | 46.5 | 27.7 |
| 135 | 62.3 | 51.1 | 35.1 |
| 150 | 65.1 | 54.2 | 39.9 |
| 165 | 67.7 | 54.0 | 41.3 |
| 180 | 69.9 | 53.4 | 42.2 |

The most drastic changes in slope for all three embodiments occurs between 0 degrees to about 60 degrees. In this portion, the rate of change of the angles is far more rapid. Whereas, between 60 degrees to about 180 degrees, the rate of change of the angle of the frustum portion is comparatively slow. The portion between 0 and 60 degrees is the area which is often the most problematic with respect to sealing due to the correspondingly complex geometry of the user's face in this portion. This is further complicated by the fact that this portion of the face also has little soft tissue. To compensate for this problem, the present invention provides a flap that extends towards the face of the user with a greater angle in these portions to preload this portion of the cushion as the mask is placed on the face of the user. However, in the portions where sealing is not as great of an issue, the rate of change of the angle of the frustum-shaped portion is much gentler to maximize comfort.

An alternative embodiment of the present invention is depicted in FIGS. 14-19. This embodiment is similar to the previous embodiments. Yet, unlike the previous embodiments, the present embodiment is a low profile cushion configured to fit closely about the tip of the nose. Specifically, this embodiment of the invention provides a cushion 300 which has a generally triangular-shaped body 302 configured to contact the face of the user and provide a fluid-tight seal so that the gas supplied by the gas source may be communicated to the user. Generally, the body has an apex region 304 and corner regions 306. Extending between the apex region 304 and corner regions 306 are side regions 308, and extending between corner regions 306 is base region 310. The body also has a coupling portion 312 configured to couple the cushion to the shell and a flap portion 316 configured to contact the face of the user. Between the flap portion 316 and the coupling portion 312 is a middle portion 314 configured to provide clearance between the flap portion and the coupling portion. The coupling portion is substantially cylindrical in this embodiment. However, the coupling portion 312 may have a variety of other shapes. In addition, the coupling portion may include an alignment feature, not shown, to align the cushion with the shell. For instance, the cushion and shell may have tabs and corresponding recesses to align the cushion. Furthermore, the cushion is described as being attached to a shell. However, the cushion may be attached directly to conduit 42 or conduit coupling 48. To further distinguish between the various other portions of the mask, the middle portion includes a middle apex portion 326, middle corners 328, middle sides 330 and a middle base 332. The flap portion includes a flap apex portion 334, flap corner portions 336, flap side portions 338, and a flap base portion 340.

Flap portion 316 has a shoulder 354 which is configured to roughly conform to the facial features of a user about the nasal portion to enhance the seal with the face of the user. The shoulder forms an annular ring about the cushion and traces a nonlinear path that roughly conforms to the complex geometry of the user's face. When viewed from the side, the shoulder defines an apex-proximal flap surface 356, a central flap surface 358, and a base proximal flap surface 360. Angle 364 of the central flap surface 356 is acute and preferably approximately zero. Angle 362 of the apex-proximal flap surface and angle 366 of the base-proximal flap surface 360 are also acute; however angle 366 and angle 362 are greater than angle 364. As shoulder passes around and in to the apex region 304 and base portion 310, the shoulder defines an apex flap surface 367 and a base flap surface 368. The apex flap surface comes to a rounded point in the apex region while the base flap surface has a low flat U-shaped configuration in the base portion.

Figure 14:
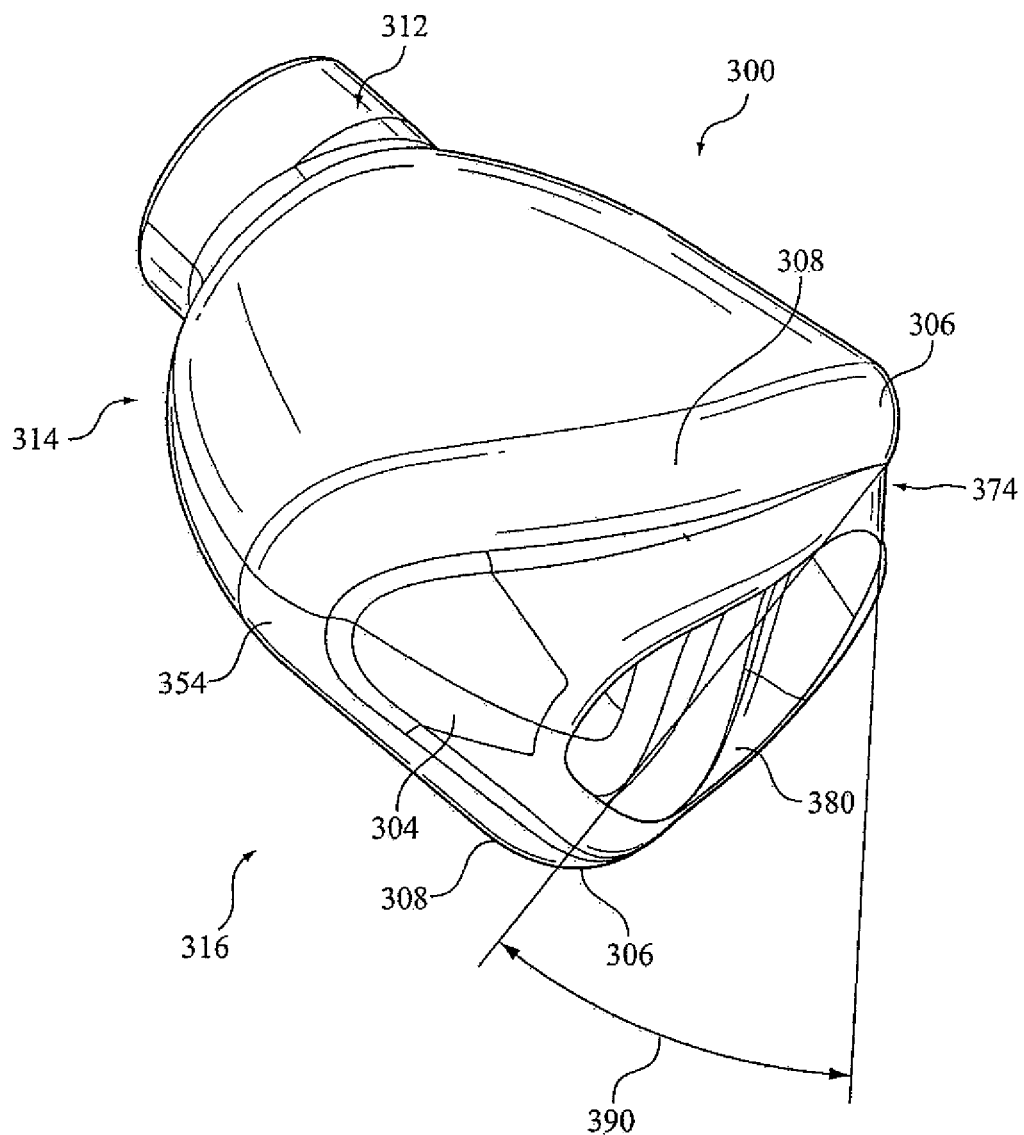
FIG. 14 is a perspective view of a fourth embodiment of the cushion.
Figure 15:
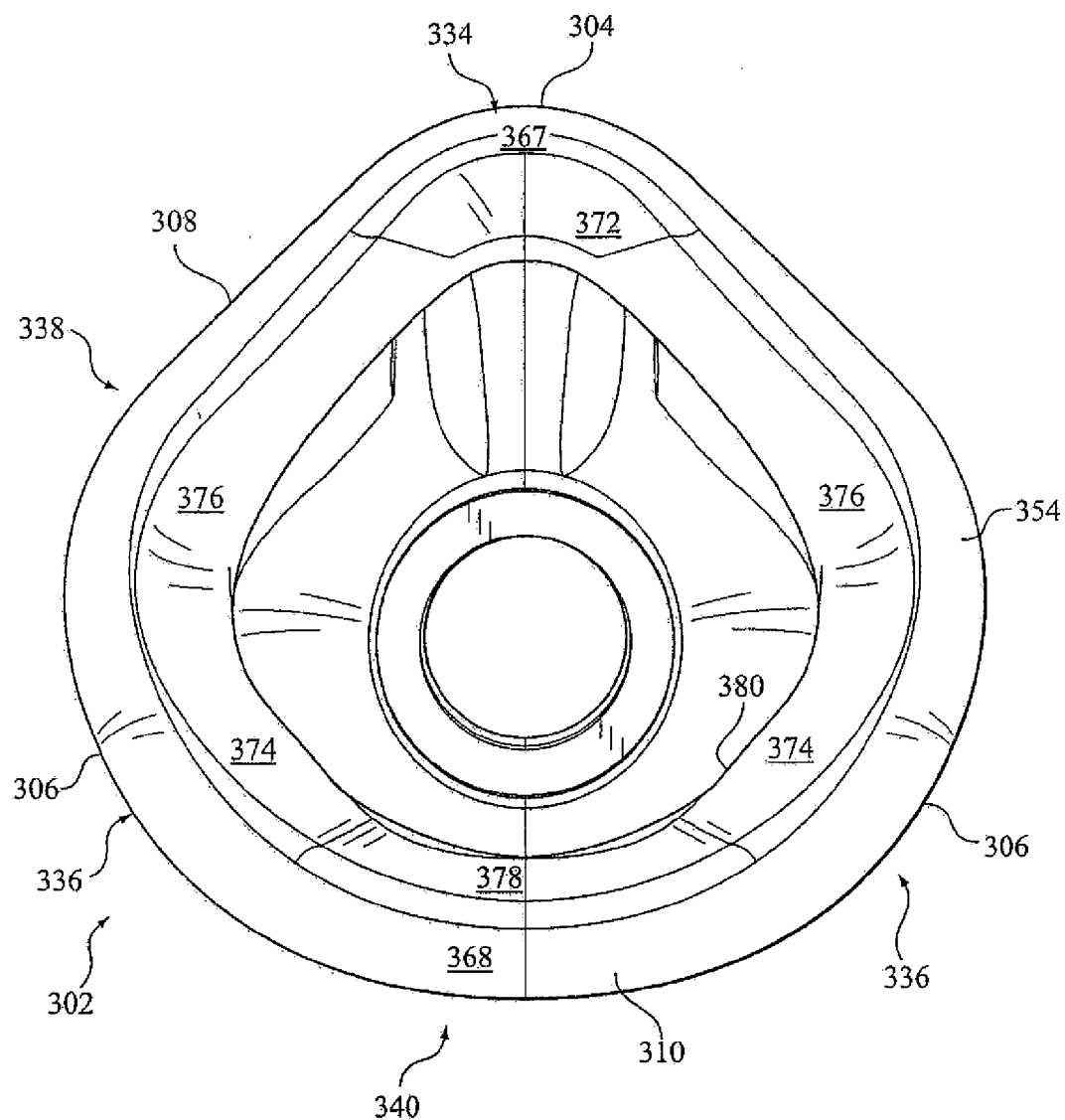
FIG. 15 is a bottom plan view of the cushion of FIG. 14.
Figure 16:
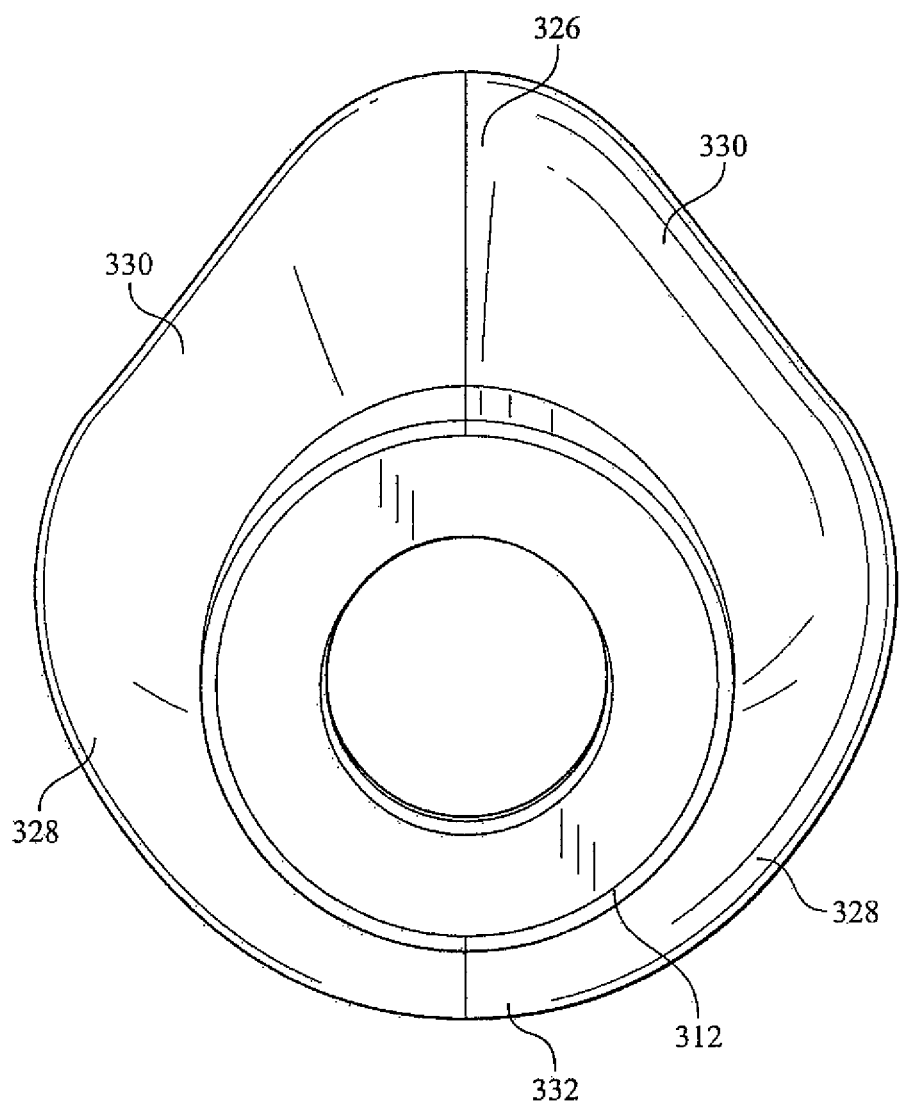
FIG. 16 is a top plan view of the cushion of FIG. 14.
Figure 17:
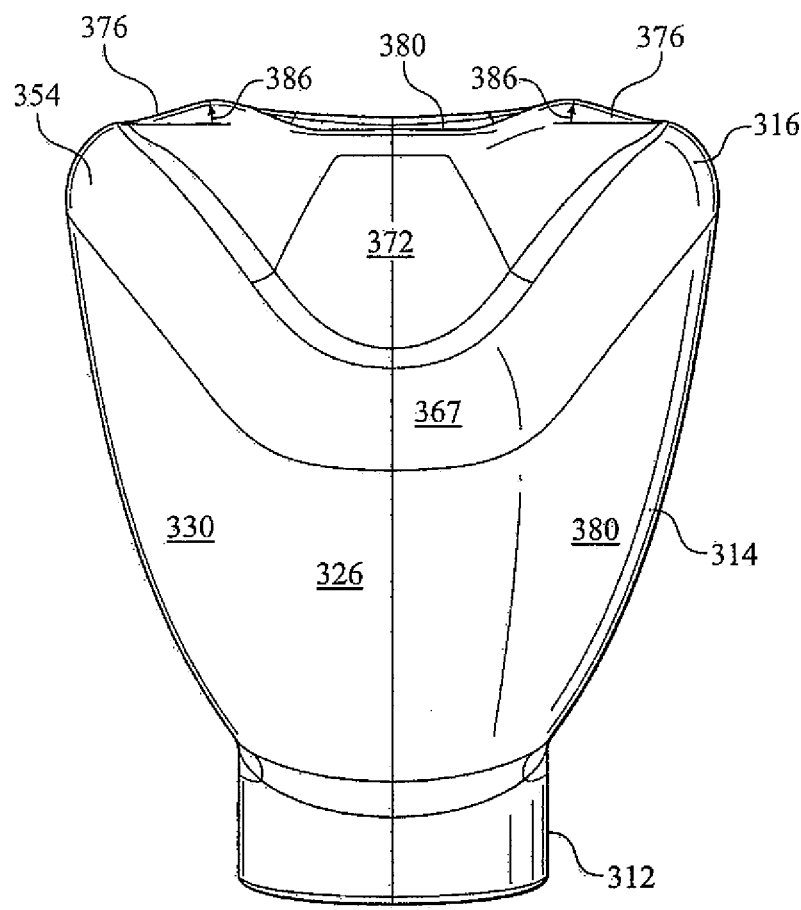
FIG. 17 is a front elevational view of the cushion of FIG. 14.
Figure 18:
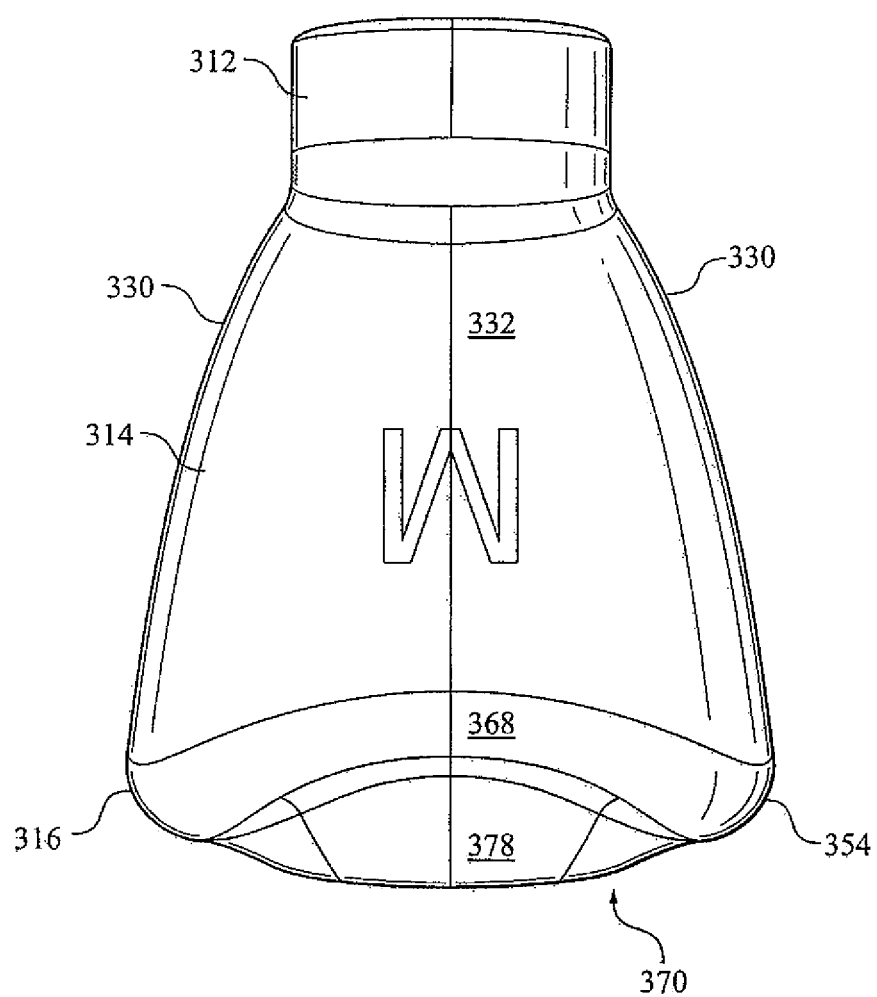
FIG. 18 is a rear elevational view of the cushion of FIG. 14.
Figure 19:
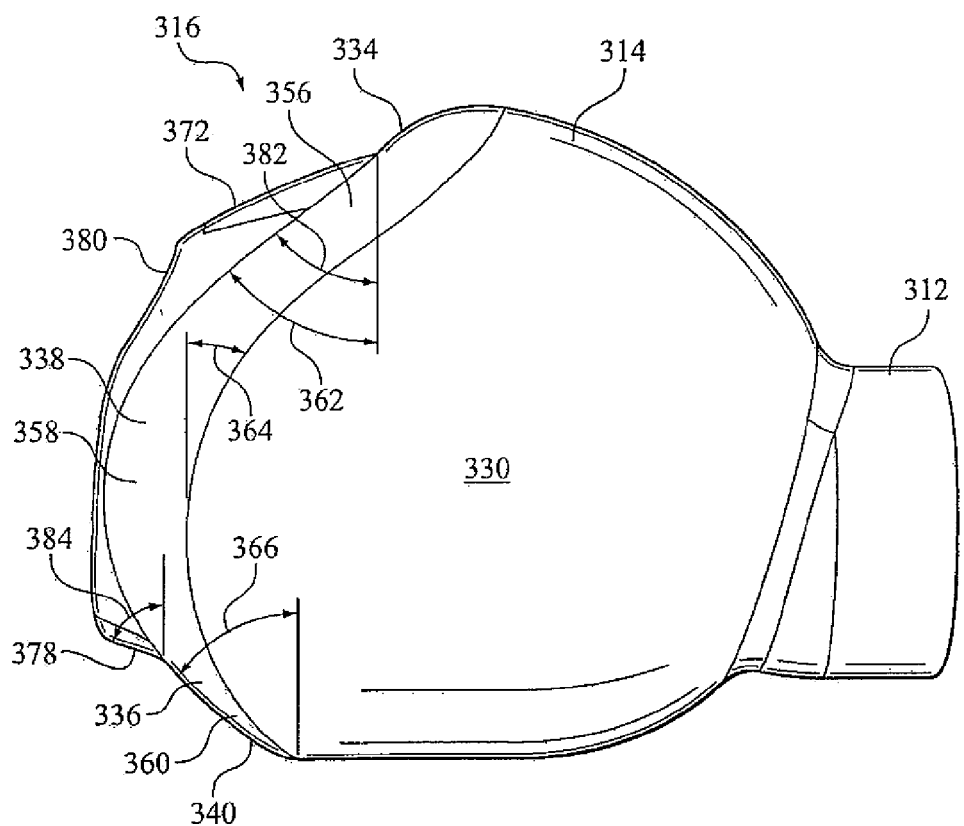
FIG. 19 is a side elevational view of the cushion of FIG. 14.

The flap portion of the present invention also includes a frustum-shaped portion 370 extending from shoulder 354 and terminating at opening 380 whereas prior art cushions have flap portions that terminate at the shoulder which extends approximately normal to the face of the user a short distance from the periphery of the cushion. The frustum-shaped portion extends from the shoulder and has a frustum-like shape. The frustum-shaped portion may have a variety of geometric shapes. For instance, in the present embodiment, the frustum-shaped portion has a frusta-pyramidal shape defined by a frusta-apex 372, frusta-corners 374, frusta-sides 376 and a frusta-base 378. As seen in FIGS. 14, 17, and 19, frusta-apex 372 extends at an angle 382; frusta-base 378 extends at an angle 384; frusta-sides 376 extend upward at an angle 386; and frusta-corners 374 extend upward at an angle 390. These angles are shown measured from the midpoint of each respective region. Of course, the angles smoothly transition from each angle to the next angle in the corresponding adjacent region.

Although sharing several of the unique features as the previous embodiments, this embodiment utilizes a frustum-shaped portion that utilizes different, and comparatively larger angled portions which are deemed advantageous in a low profile device. Of course, the angles could be different than those shown. This embodiment utilizes a cushion that is configured to minimize the interface between the cushion and the face of the user both with respect to the surface area of the face enclosed and with respect to the amount of flap that contacts the user's face. To enhance these cushions, it has been found to be desirable to utilize a frustum-shaped portion that extends towards the face of the user with a larger angle to enhance preloading of the cushion as the nose of the user is inserted.

An alternative embodiment of the present invention is depicted in FIGS. 20-24. The present embodiment is similar to the previous embodiment. Yet, unlike previous embodiments, the present embodiment is a cushion configured to fit over the mouth and nose of the user rather than merely the nose. Specifically, the present invention provides a cushion 400 which has a generally triangular-shaped body 402 configured to contact the face of the user and provide a fluid-tight seal so that the gas supplied by the gas source may be communicated to the user. Generally, the body has an apex region 404 and corner regions 406. Extending between the apex region 404 and corner regions 406 are side regions 408 and extending between corner regions 406 is base region 410. The body also has a coupling portion 412 configured to couple the cushion to the shell and a flap portion 416 configured to contact the face of the user. Between the flap portion 416 and the coupling portion 412 is a middle portion 414 configured to provide clearance between the flap portion and the coupling portion. To further distinguish between the various portions of the mask, the coupling portion includes a coupling apex portion 418, coupling corner portions 420, coupling side portions 422, and coupling base portion 424. The middle portion includes a middle apex portion 426, middle corners 428, middle sides 430 and a middle base 432. The flap portion includes a flap apex portion 434, flap corner portions 436, flap side portions 438, and a flap base portion 440.

Figure 23:
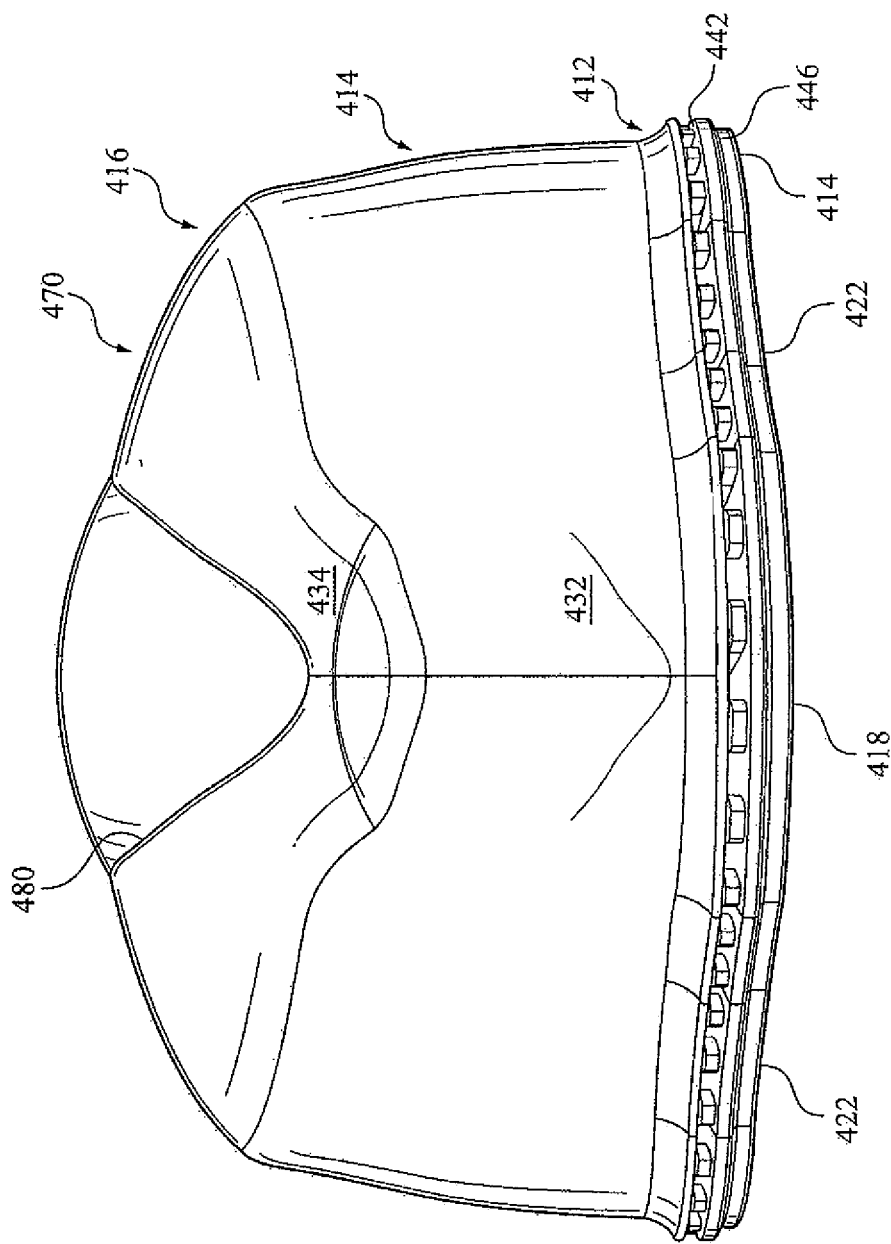
FIG. 23 is a front elevational view of the cushion of FIG. 20.

As seen in FIG. 23, the coupling portion of the cushion has a collar 442 having a plurality of serrations. Adjacent the collar is a lip 444 radially spaced inwardly by an undercut 446 which seals with the insert. The insert, in turn, seals against the shell. Alternatively, in some embodiments, the insert may be omitted. If omitted, the lip may be configured to seal directly against the body of the shell. The middle side portion of the cushion has a generally dome-shaped configuration extending between the coupling side portion and the flap side portion. The sides 430 have an apex-proximal portion 448, a central portion 450, and a base-proximal portion 452. The height middle sides 430 extend away from coupling portion 412 is greater in the central portion 450 than in the apex-proximal portion 448 or the base-proximal portion 452.

Figure 20:
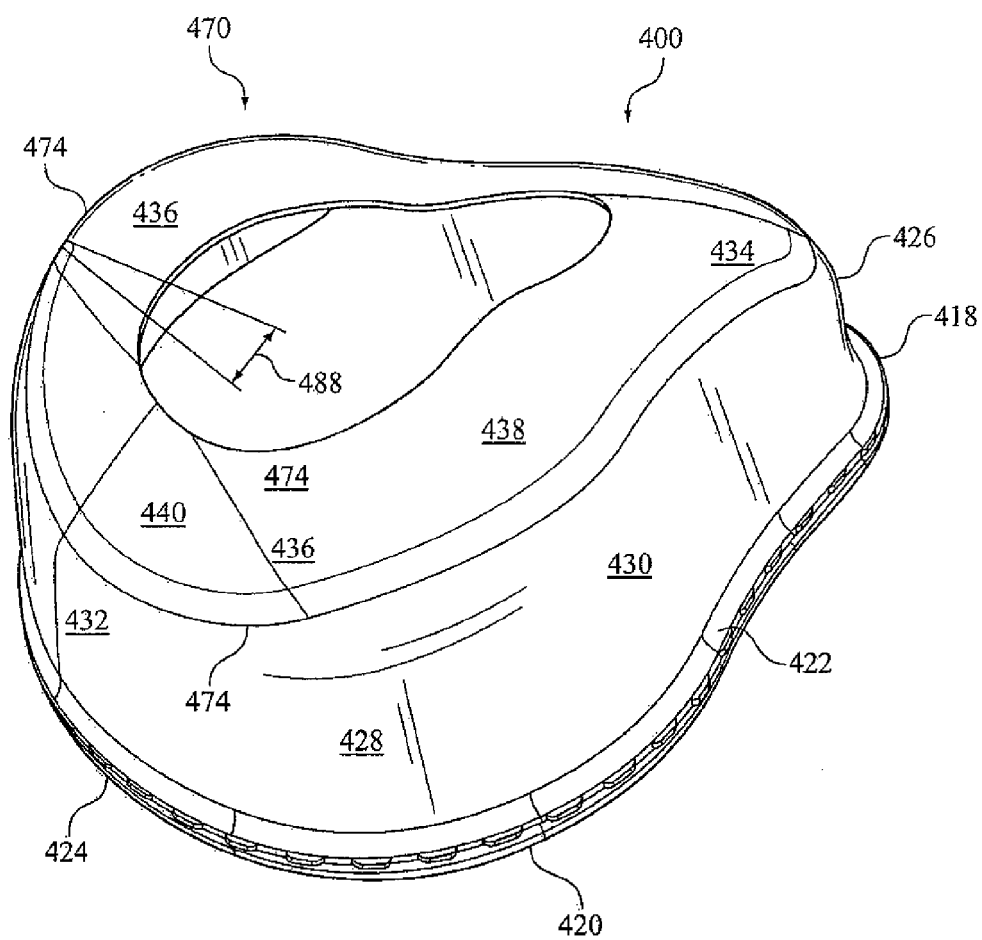
FIG. 20 is a perspective view of a fifth embodiment of the cushion.
Figure 21:
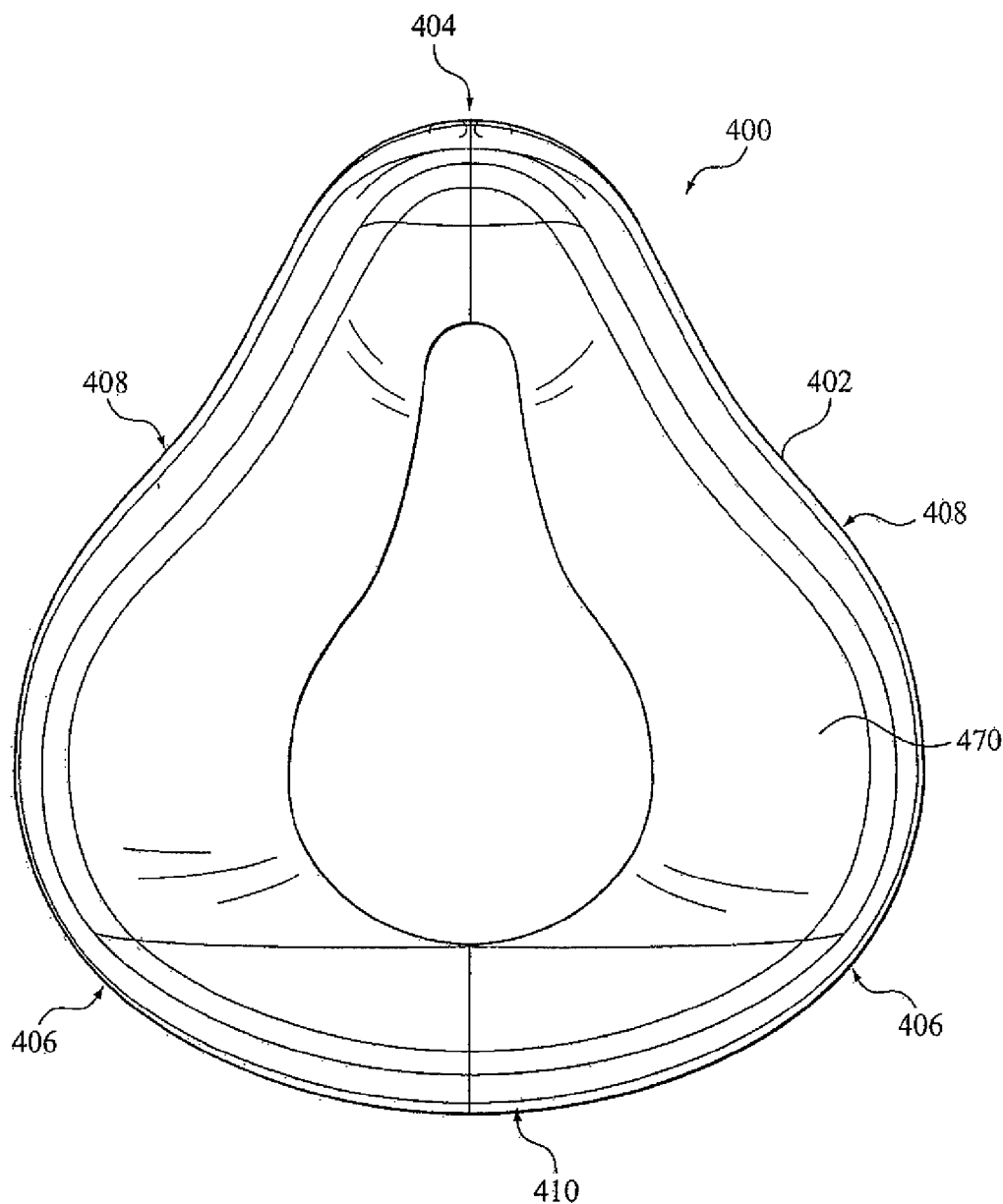
FIG. 21 is a top plan view of the cushion of FIG. 20.
Figure 22:
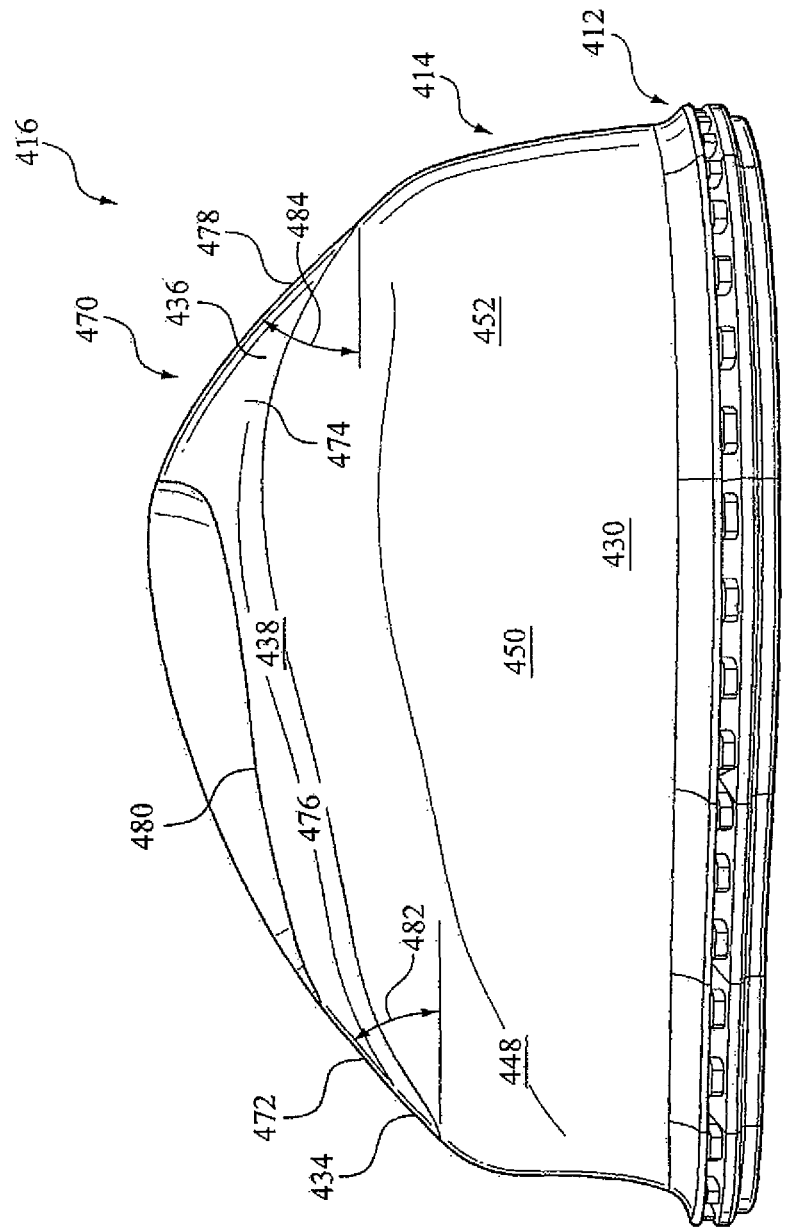
FIG. 22 is a side elevational view of the cushion of FIG. 20.
Figure 24:
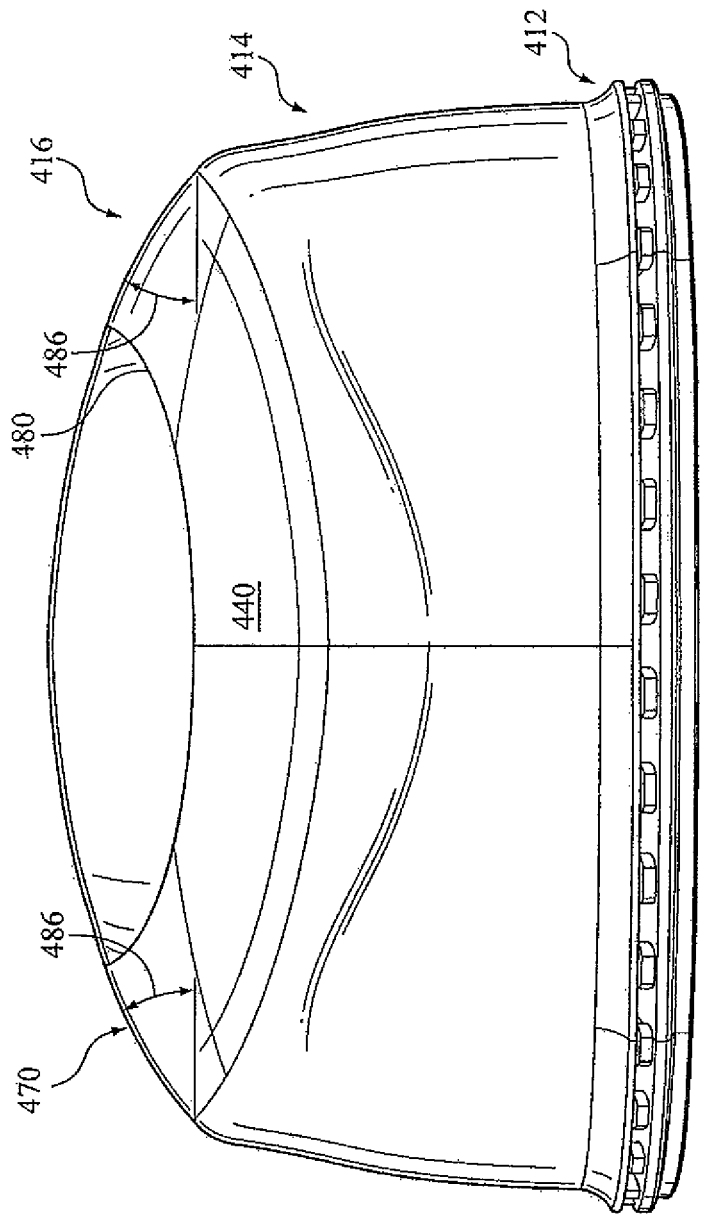
FIG. 24 is a rear elevational view of the cushion of FIG. 20.

The flap portion 416, in this embodiment, has a single continuous frustum-shaped flap portion 470 extending from the middle portion 414 and terminating at opening 480. The frustum-shaped portion may have a variety of geometric shapes. For instance, in the present embodiment, the frustum-shaped portion has a frusta-pyramidal shape defined by a frusta-apex 472, frusta-corners 474, frusta-sides 476 and a frusta-base 478. As seen in FIGS. 20, 22, and 24, frusta-apex 472 extends at an angle 482; frusta-base 478 extends at an angle 484; frusta-sides 476 extend upward at an angle 486; frusta-corners 474 extend at an angle 488. These angles are shown measured from the midpoint of each respective region. Of course, the angles smoothly transition from each angle to the next angle in the corresponding adjacent region.

Figure 25:
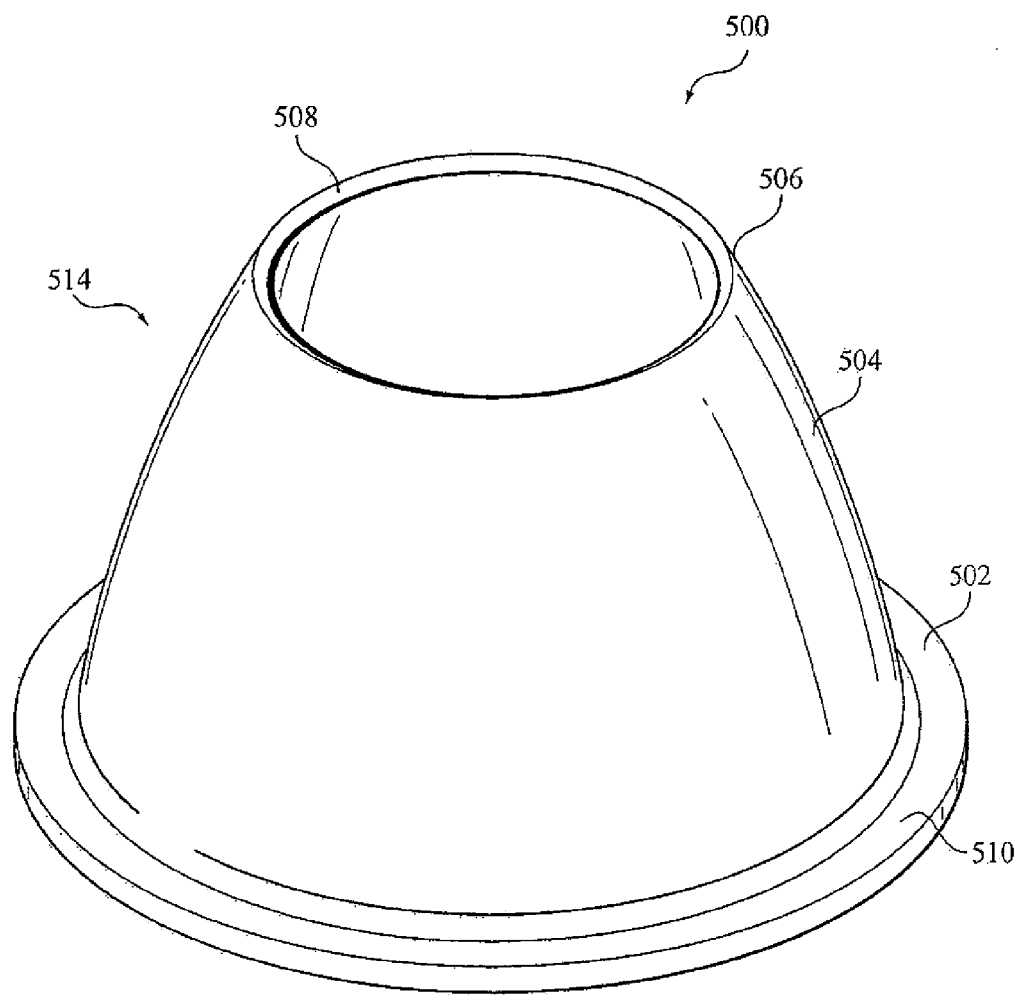
FIG. 25 is a perspective view of a sixth embodiment of the cushion.
Figure 26:
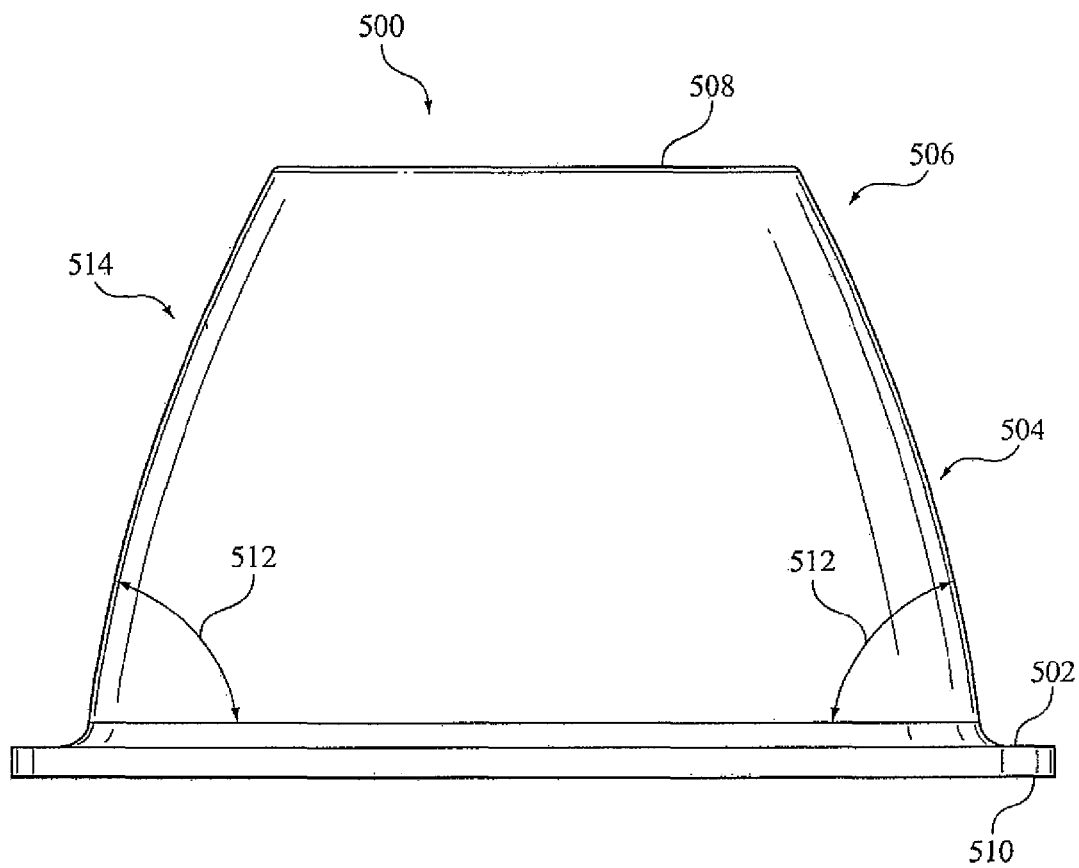
FIG. 26 is an elevational view of the cushion of FIG. 25.

Another alternative embodiment of the present invention is depicted in FIGS. 25 and 26. Cushion 500 shown in this embodiment has a generally frusta-conical shape rather than the frusta-pyramidal shape of the previous embodiment. This embodiment provides a more simplistic geometric shape which may result in manufacturing efficiencies. Specifically, the present embodiment includes a coupling portion 502, a middle portion 504, and a flap portion 506 terminating at an opening 508. The coupling portion includes a collar 510. The middle portion 504 and flap portion 506 smoothly transition into one another. Nonetheless, the flap portion of this embodiment still contacts the face of the user while the middle portion still spaces the flap portion from the coupling portion. The cushion 500 extends upward and slightly inwardly at an acute angle 512. Angle 512 is approximately 75 degrees. Of course, a variety of other angles may be utilized.

Figure 27:
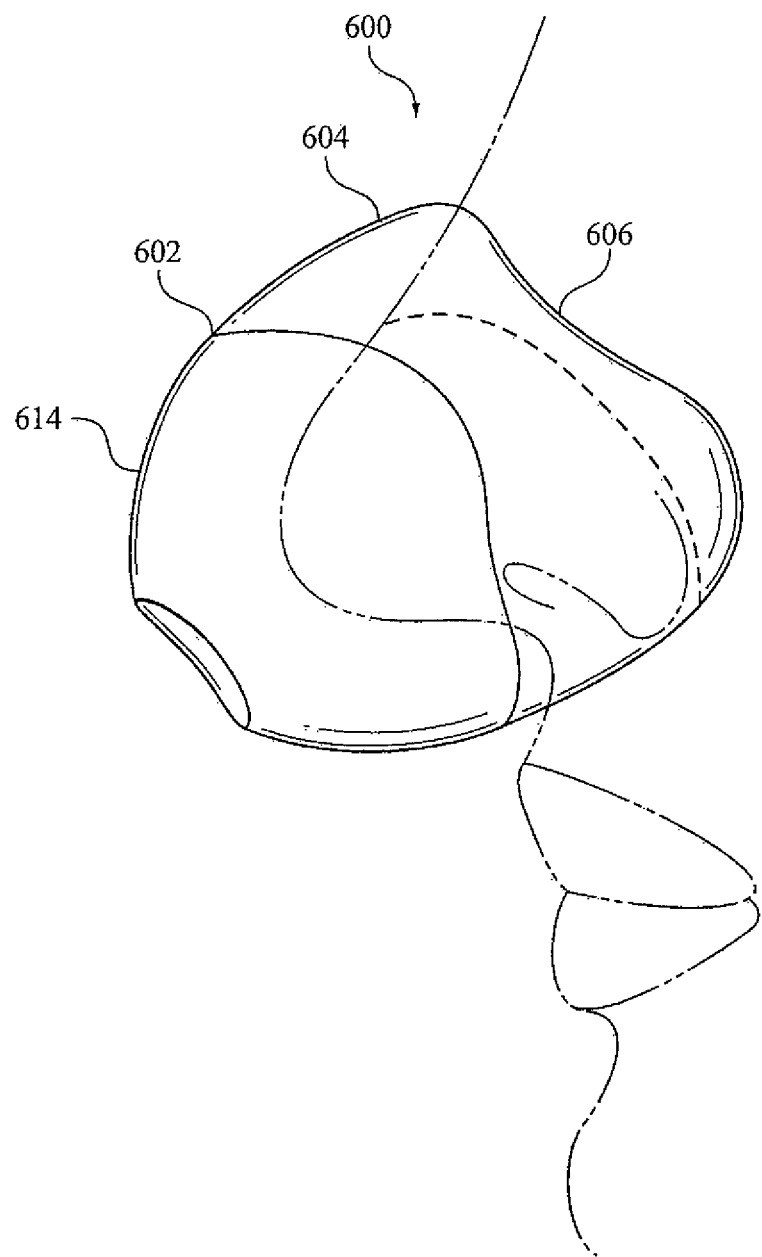
FIG. 27 is a side elevational view of a seventh embodiment of the mask located on the face of a patient.
Figure 28A:
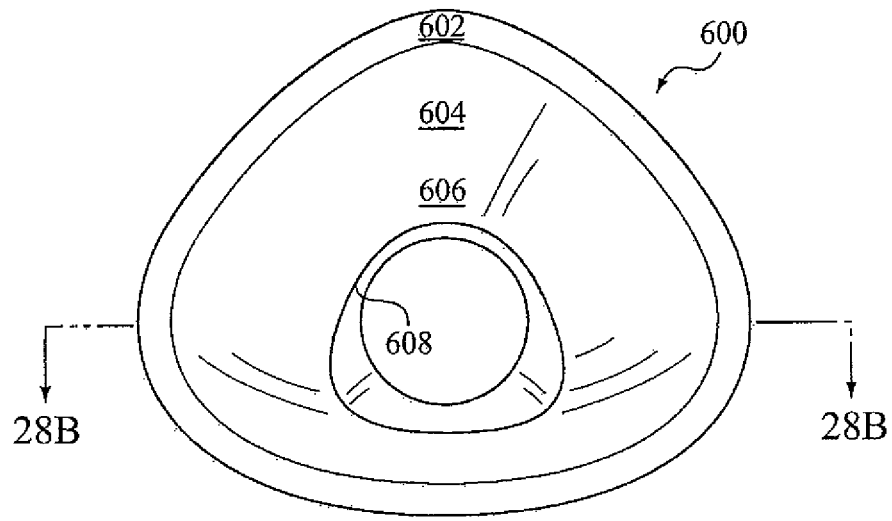
FIGS. 28A and 28B are a top plan view and a cross-sectional view of the mask of FIG. 27.
Figure 28B:
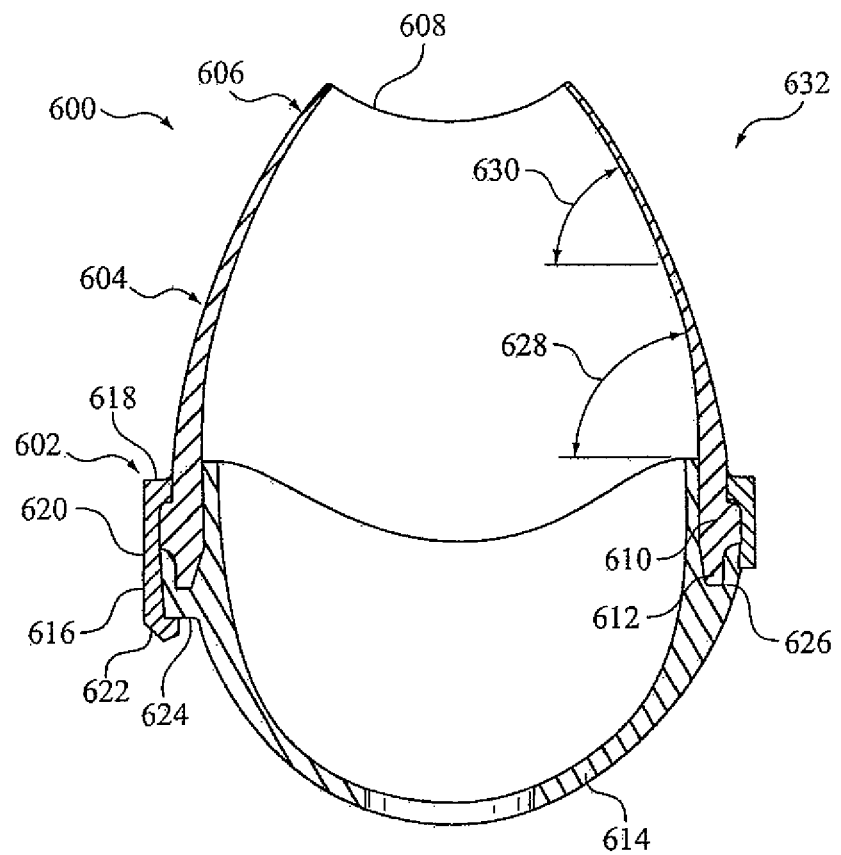

Another alternative embodiment of the present invention is shown in FIGS. 27-28B. This embodiment depicts a cushion 600 having a generally frusta-conical shape. The cushion includes a coupling portion 602, a middle portion 604, and a flap portion 606. The entire cushion 600 has a frusta-conical shape 632 terminating at an opening 608. The coupling portion includes a collar 610 and a lip 612. The cushion is configured to be coupled to a shell 614 by a retention ring 616. Retention ring 616 includes a top surface 618 and a skirt 620. The skirt includes a ledge 622 which engages surface 624. Sandwiched between the retention ring and the shell is the cushion. The shell includes a groove 626 configured to receive lip 612. The present embodiment has a wall thickness that varies and curves inwardly becoming more acute. The middle portion has a wall thickness that is thicker than the wall thickness of the flap portion. In an exemplary embodiment, the wall thickness of middle portion 604 is approximately 0.020 to 0.035 inches, and wall thickness of flap portion 602 is approximately 0.005 to 0.010 inches. In addition, the angle the middle portion and flap portion extend varies. The middle portion extends at an angle 628 approximately normal to the coupling portion while the flap portion extends at an angle 630. In one embodiment of the present invention, angle 628 of the middle portion is approximately 85 degrees and angle 630 of the flap portion is approximately 60 degrees.

Figure 29:
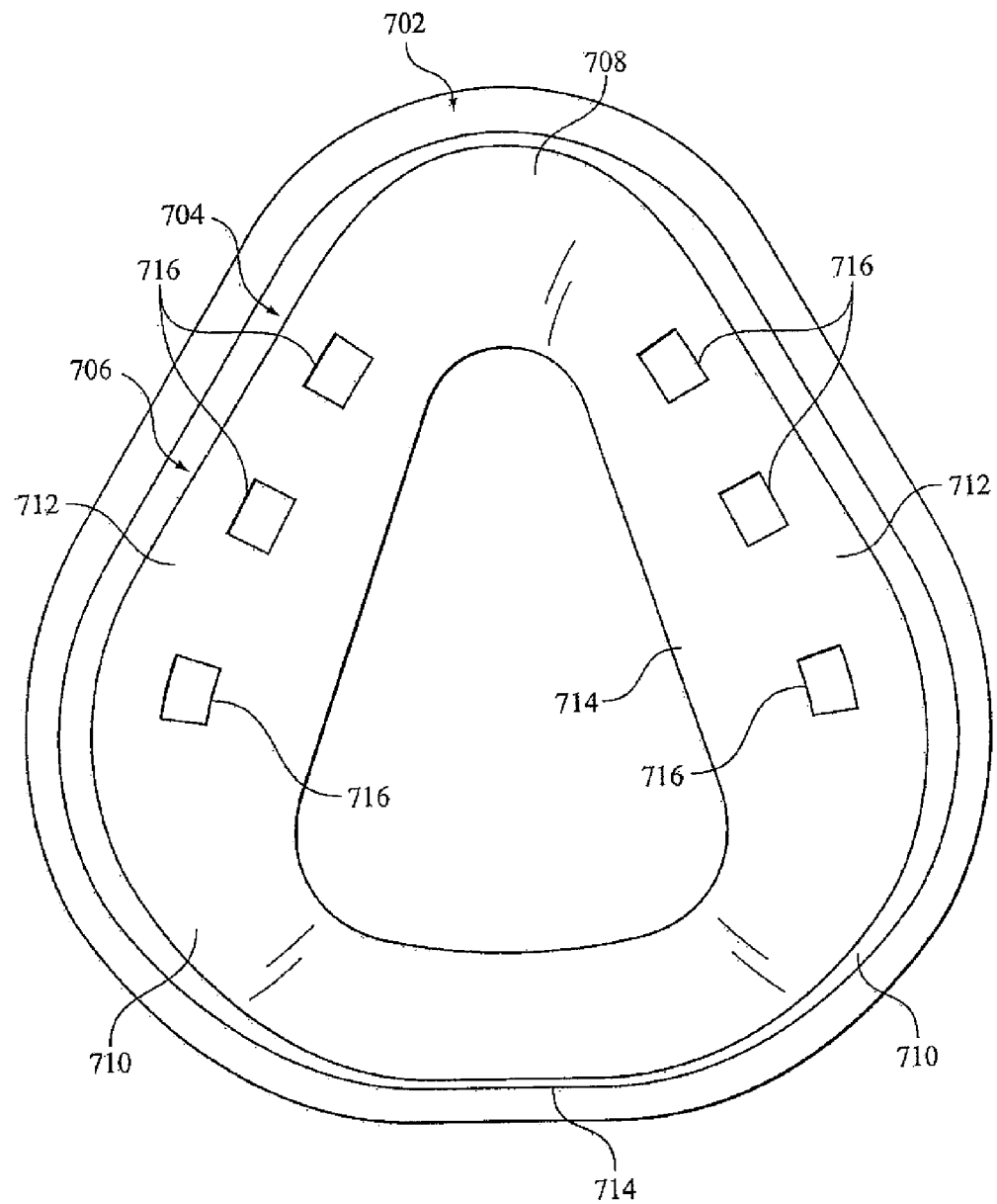
FIG. 29 is a top plan view of an eight embodiment of the cushion.

Another alternative embodiment is shown in FIG. 29. As shown, the cushion 700 has a coupling portion 702, a middle portion 704, and a flap portion 706. The flap portion includes an apex region 708, corner regions 710. Between the apex region 708 and the corner regions 710 are side regions 712. Between corner portions 710 is base portion 714. The flap extends from middle portion 704 to opening 714. One additional unique feature of this embodiment is that the flaps include apertures 716. A single aperture 716 may be used or multiple apertures 716 may be used about the flap portion 704. Moreover, the apertures may have a variety of shapes without departing from the scope of the present invention. The apertures may be placed closer towards the middle portion 704 or closer to opening 714. It has been found that in cushions with elongate flap portions, such as those described in the present application, that as the flaps roll inwardly a small channel may form between the inner and outer portions of the flap resulting in a small venturi between the inner and outer portions of the flap. As air is accelerated between these two surfaces, the flexible walls cyclically collapse and expand resulting in undesirable vibrations and noise. Incorporation of apertures 716 along one or both surfaces has been found to reduce the tendency of these portions to vibrate or make noise.

Generally, the cushions of the present invention may be constructed from a variety of materials such as but not limited to Silicon. The material may have a durometer of between 10-80 Shore A. The material may have a durometer of approximately 40 Shore A. To further enhance the conformability of the cushion, the wall thickness may be varied. The wall thickness may be between approximately 0.001 inch to 0.05 inch. In addition, the wall thickness may be varied to create regions of comparative rigidity or flexibility, as shown in FIG. 28B.

In accordance with the various embodiments of the present invention, the cushion may be shaped to have anatomical features as shown in FIGS. 1-24, and 29; or, the cushion may be formed without anatomical features as shown in FIGS. 25-28. Common to both embodiments is the frustum-shaped flap portion. As best appreciated by one of ordinary skill in the art, a cushion which is preset with particularly desirable anatomical features may more easily conform to the facial characteristics of the user. Alternatively, a cushion which lacks anatomical features may not start with an appropriate anatomical shape; yet, such a cushion does not have preset features which may be incompatible with the facial characteristics of a particular user. Accordingly, such cushions may accommodate a larger number of users with differing facial characteristics. Any suitable material may be utilized within the scope of the present invention. However, in the event that the cushion is formed with a particular shape, it would be desirable to utilize a material which is, at least partially, elastically deformable. Elastically deformable materials regain their pre-stressed configuration once an applied force has been removed. Alternatively, the cushion may be formed from a material that is, at least partially, plastically deformable such that it has little or no shape memory. This may be a desirable characteristic in the event that the cushion is formed without anatomical characteristics. As the cushion deforms to correspond to the facial characteristics of the user, the cushion does not have to overcome incompatible preset features.

With respect to the angles referenced herein, all of the angles described were measured from a common datum plane which was displaced from but coplanar with the coupling portion. However, these angles could be measured from an alternative datum such as a plane running through the middle portion, flap portion, or any other suitable datum so that the relative angles of each portion can be compared with one another. Of course, should the unique aspects of the present invention be utilized in other masks such as a full face mask which covers the mouth and nose of the user, a total mask which covers the entire face of the user, or nasal cushions which abut nose of the user, or any other mask, the shape of the cushion can be altered to conform to the geometric shape of the different anatomical regions with corresponding changes in the angles of each region.

In use, the user of an embodiment of the present invention will place the cushion on their face and compress the mask to make a seal. The mask is secured on the face of the user by a headgear assembly. The shell in turn is coupled to the gas source via the conduit coupling. Due to the unique frustum portion of the cushion, as a force is applied to the flap portion, the flap portion smoothly rolls inwardly to form a seal with the patient's face. This configuration minimizes ripples or creases that result in discomfort or potentially compromise the seal integrity with the face of the user.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. In addition, specific features of this invention are shown in some drawings and not others, this is for convenience only as each feature may be combined with any or all of the other features in accordance with the invention. Other embodiments will occur to those skilled in the art and are within the following claims:

What is claimed is:

1. A cushion for use in a respiratory mask having a shell, the cushion comprises:
    a coupling portion for coupling the cushion to the shell, the coupling portion having a first end portion defining a first opening in a first plane and a second end portion opposite the first end portion, the cushion having a central axis that extends through the first opening in a direction from the first end of the coupling portion through the second end of the coupling portion;
    a middle portion extending from the coupling portion to provide clearance from the coupling portion, the middle portion having a bottom portion adjacent and connected to the second end portion of the coupling portion and a top portion opposite the bottom portion; and
    a flap portion configured to form a seal with a face of a user, the flap portion including a shoulder portion defined by a first terminal end directly coupled to the top portion of the middle portion and a second terminal end opposite the first terminal end, the shoulder portion extending continuously inwardly toward the central axis from the first terminal end to the second terminal end and defining a generally annular ring about the cushion that traces a nonlinear path and that is configured to contact the face of the user, and a frustum-shaped portion defined by a third terminal end directly coupled to the second terminal end of the shoulder portion and a fourth terminal end opposite the third terminal end, the frustum shaped portion extending both continuously inwardly toward the central axis from the third terminal end to the fourth terminal end and continuously outwardly in a direction away from the coupling portion as determined from the third terminal end to the fourth terminal end, wherein no part of the cushion extends directly from the fourth terminal end away from the frustum-shaped portion toward the coupling portion and the fourth terminal end of the frustum-shaped portion defines a second opening that is smaller than the first opening and that is non-coplanar with and located a non-zero distance above the middle portion, wherein at least a portion of the second opening is located further along the central axis from the coupling portion than any part of the shoulder portion, wherein the frustum-shaped portion comprises:

an apex region, corner regions, side regions extending between the apex region and the corner regions, and a base region extending between the side regions, wherein the frustum-shaped portion extends away from the top portion of the middle portion in the direction away from the coupling portion at an angle with respect to a second plane through the top portion of the middle portion that is parallel to the first plane, and wherein a rate of change of the angle about 60 degrees on either side of the apex region changes from negative to positive.

2. The cushion as recited in claim 1, wherein the second opening is located at least ⅛ inch above the middle portion such that the frustum-shaped portion contacts the face of a user and rolls inwardly to preload the cushion.

3. The cushion as recited in claim 2, wherein the frustum-shaped portion is frusta-conical in shape.

4. The cushion as recited in claim 2, wherein the frustum-shaped portion is frusta-pyramidal in shape.

5. The cushion as recited in claim 1, wherein in at least a portion of the cushion the shoulder portion extends at a first angle with respect to the first plane and the frustum-shaped portion extends at a second angle with respect to the first plane, the second angle being greater than the first angle.

6. The cushion as recited in claim 5, wherein in the at least a portion of the cushion at least a portion of the shoulder portion is parallel to the first plane.

* * * * *